US011584914B2

(12) United States Patent
Jenkinson et al.

(10) Patent No.: US 11,584,914 B2
(45) Date of Patent: Feb. 21, 2023

(54) **PROCESSES FOR PRODUCING ORGANIC SOLVENTS USING *CLOSTRIDIUM SACCHAROPERBUTYLACETONICUM***

(71) Applicant: Biocleave Limited, Abingdon (GB)

(72) Inventors: Elizabeth Jenkinson, Abingdon (GB); Amanda J. Nicolle, Abingdon (GB); Aretha N. Atmadjaja, Didcot (GB)

(73) Assignee: Biocleave Limited, Oxfordshire (GB)

( * ) Notice: Subject to any disclaimer, the term of this patent is extended or adjusted under 35 U.S.C. 154(b) by 0 days.

(21) Appl. No.: 16/755,010

(22) PCT Filed: Oct. 12, 2018

(86) PCT No.: PCT/GB2018/052937
§ 371 (c)(1),
(2) Date: Apr. 9, 2020

(87) PCT Pub. No.: WO2019/073254
PCT Pub. Date: Apr. 18, 2019

(65) Prior Publication Data
US 2021/0189325 A1 Jun. 24, 2021

(30) Foreign Application Priority Data
Oct. 13, 2017 (GB) .................................. 1716845

(51) Int. Cl.
| | | |
|---|---|---|
| C12N 1/20 | (2006.01) | |
| C07K 14/32 | (2006.01) | |
| C12N 1/04 | (2006.01) | |
| C12P 7/06 | (2006.01) | |
| C12P 7/16 | (2006.01) | |
| C12P 7/28 | (2006.01) | |
| C12P 7/52 | (2006.01) | |
| C12P 7/56 | (2006.01) | |
| C12R 1/145 | (2006.01) | |

(52) U.S. Cl.
CPC ................ *C12N 1/20* (2013.01); *C07K 14/32* (2013.01); *C12N 1/04* (2013.01); *C12N 1/205* (2021.05); *C12P 7/065* (2013.01); *C12P 7/16* (2013.01); *C12P 7/28* (2013.01); *C12P 7/52* (2013.01); *C12P 7/56* (2013.01); *C12R 2001/145* (2021.05)

(58) Field of Classification Search
None
See application file for complete search history.

(56) References Cited

U.S. PATENT DOCUMENTS

| | | | |
|---|---|---|---|
| 4,521,516 A | 6/1985 | Lemme et al. | |
| 4,613,570 A | 9/1986 | Zeman | |
| 5,192,673 A | 3/1993 | Jain et al. | |
| 5,501,968 A | 3/1996 | Starnes et al. | |
| 5,753,474 A | 5/1998 | Ramey | |
| 8,084,243 B2 | 12/2011 | Bennett et al. | |
| 2011/0296747 A1 | 12/2011 | Sonomoto et al. | |
| 2012/0276606 A1 | 11/2012 | Okabayashi et al. | |
| 2015/0368678 A1* | 12/2015 | Jenkinson ............ C12N 9/1074 | |
| | | | 435/252.7 |

FOREIGN PATENT DOCUMENTS

| | | | |
|---|---|---|---|
| CN | | 106636168 A | 5/2017 |
| JP | | 2014 042472 A | 3/2014 |
| WO | | 1989/003421 A1 | 4/1989 |
| WO | | 1991/009962 A1 | 7/1991 |
| WO | | 2007/148091 A3 | 7/2008 |
| WO | | 2008/144060 A2 | 11/2008 |
| WO | WO 2008/144060 A2 | | 11/2008 |
| WO | | 2009/101400 A3 | 10/2009 |
| WO | WO 2011/090985 A2 | | 7/2011 |
| WO | WO 2012/068310 A2 | | 5/2012 |
| WO | | 2014/122449 A1 | 8/2014 |
| WO | | 2014/122448 A4 | 11/2014 |
| WO | | 2014/207480 A2 | 12/2014 |
| WO | | 2015/159087 A1 | 10/2015 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Accession J7FTL3. Oct. 31, 2012 (Year: 2012).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Liang, Quanfeng, et al., "The effect of cyclodextrins on the ethanol tolerance of microorganisms suggests potential application," J Ind Microbiol Biotechnol (2011) 38:753-756.
Shity, Halla and Bar, Raphael, "New Approach for Selective Separationof Dilute Products from Simulated Clostridial Fermentation Broths Using Cyclodextrins," Biotechnology and Bioengineering, 39(4):462-466, Feb. 1992.
Kosaka, Tomoyuki, et al., "Characterization of the sol Operon in Butanol-Hyperproducing *Clostridium saccharoperbutylacetonicum* Strain N1-4 and Its Degeneration Mechanism," Biosci. Biotechnol. Biochem., 71(1) 58-68 (2007).
(Klaushofer and Parkkinen) Lee, et al., *Thermoanaerobacter thermohydrosulfuricus*, 53016 Product Sheet, May 20, 2021.
Beesch, Samuel C., "Acetone-Butanol Fermentation of Sugars," Industrial & Engineering Chemistry, (1952) 44(7), pp. 1677-1682.
Speakman, H.B. and Phillips, J.F., "A Study of a Bacterial Association I. The Biochemistry of the Production of Lactic Acid," J Bacteriol. 9(2):183-199 (1923).

(Continued)

*Primary Examiner* — Christian L Fronda
(74) *Attorney, Agent, or Firm* — Knobbe, Martens, Olson & Bear, LLP

(57) ABSTRACT

A process for culturing *Clostridium saccharoperbutylacetonicum* cells, which are capable of growing on gamma-cyclodextrin in a liquid culture medium in a culture vessel. Also disclosed is a process for producing a bio-product, the process comprising culturing *Clostridium saccharoperbutylacetonicum* cells, which are capable of growing on gamma-cyclodextrin in a liquid culture medium in a culture vessel.

10 Claims, 14 Drawing Sheets

Specification includes a Sequence Listing.

(56) References Cited

OTHER PUBLICATIONS

Annous, B.A., & Blaschek, H.P., "Isolation and characterization of Clostridium acetobutylicum mutants with enhanced amylolytic activity", Appl. Environ. Microbiol., 57(9), 2544-8 (1991).
Beesch, "A Microbiological Process Report—Acetone-butanol fermentation of starches," Appl. Microbiol., 1(2), 85-95 (1953).
Bi, C., Jones, S. W., Hess, D. R., Tracy, B. P. & Papoutsakis, E. T., "SpoIIE is Necessary for Asymmetric Division, Sporulation, and Expression of σF, σE, and σG but Does Not Control Solvent Production in Clostridium acetobutylicum ATCC 824". Journal of Bacteriology 193, 5130-5137 (2011).
Collins, M.D. et al., "The phylogeny of the genus *Clostridium*: proposal of five new genera and eleven new species combinations," Int. J. Syst. Bacteriol., 44(4), 812-26 (1994).
Cook, G.M. et al., "Hyperbolic growth of Thermoanaerobacter thermohydrosulfuricus (*Clostridium thermohydrosulfuricum*) increases ethanol production in pH-controlled batch culture" Applied Microbiology and Biotechnology Mar. 1994, vol. 41, Issue 1, pp. 84-89.
Jones, D.T. and Woods, D.R., "Acetone-Butanol Fermentation Revisited," Microbiol. Rev. 50: 484-524 (1986).
Jones, D.T., van der Westhuizen, A., Long, S., Allcock, E.R., Reid, S.J., & Woods, D.R., "Solvent Production and Morphological Changes in Clostridium acetobutylicum". Appl. Environ. Microbiol., 43(6), 1434-1439 (1982).
Jones, S. W., Tracy, B. P., Gaida, S. M. & Papoutsakis, E. T., "Inactivation of σF in Clostridium acetobutylicum ATCC 824 Blocks Sporulation Prior to Asymmetric Division and Abolishes σE and σG Protein Expression but Does Not Block Solvent Formation". Journal of Bacteriology, 193, 2429-2440 (2011).
Kamionka and Dahl, "*Bacillus subtilis* contains a cyclodextrin-binding protein which is part of a putative ABC-transprter," FEMS Microbiol. Letts. 204, 55-60 (2001).
Larsen, K., "Large Cyclodextrins," Journal of Inclusion Phenomena and Macrocyclic Chemistry, vol. 43: 1-13 (2002).
Lee, Y.-E., et al., "Taxonomic Distinction of Saccharolytic Thermophilic Anaerobes: Description of *Thermoanaerobacterium xylanolyticum* gen. nov., sp. nov., and *Thermoanaerobacterium saccharolyticum* en. nov., sp. nov.; Reclassification of Thermoanaerobium brockii, Clostridium thermosulfurogenes, and Clostridium thermohydrosulfuricum E100-69 as *Thermoanaerobacter brockii* comb, nov., *Thermoanaerobacterium thermosulfurigenes* comb, nov., and *Thermoanaerobacter thermohydrosulfuricus* comb, nov., Respectively; and Transfer of Clostridium thermohydrosulfuricum 39E to Thermoanaerobacter ethanolicus." Int. J. Syst. Bacteriol., 43: 41-51 1993.
Marchini et al. "Cyclodextrins for growth of Helicobacter pylori ad production of vacuolating cytotoxin," Arch. Microbiol. 164: 290-293 (1995).
Mukai et al., "Purification, Characterization, and Gene Cloning of a Novel Maltosyltransferase from an Arthrobacter globiformis Strain that produces an Alternating α-1,4- and α-1,6-Cyclic Tetrasaccharide from Starch," Appl. Environ. Microbiol., 72(2): 1065-71 (2006).

Sandoval, N.R., et al. "Whole-genome sequence of an evolved *Clostridium pasteurianum* strain reveals Spo0A deficiency responsible for increased butanol production and superior growth". Biotechnol Biofuels 2015; 8:227.
Scotcher, M. C. & Bennett, G. N., "SpoIIE Regulates Sporulation but Does Not Directly Affect Solventogenesis in Clostridium acetobutylicum ATCC 824". Journal of Bacteriology 187, 1930-1936 (2005).
Shi & Blaschek, "Transcriptional analysis of *Clostridium beijerinckii* NCIMB 8052 and the hyper-butanol-producing mutant BA101 during the shift from acidogenesis to solventogenesis". Appl. Environ. Microbiol., 74(24); 7709-7714 (2008).
Stackebrandt, E. et al., "Phylogenetic basis for a taxonomic dissection of the genus *Clostridium*" FEMS Immunol. Med. Microbiol., 24: 253-258 (1999).
Tracy, B. P. et al. "Inactivation of σE and σG in Clostridium acetobutylicum Illuminates Their Roles in Clostridial-Cell-Form Biogenesis, Granulose Synthesis, Solventogenesis, and Spore Morphogenesis". Journal of Bacteriology 193: 1414-1426 (2011).
Watanabe, H. et al., "Cloning, Sequencing, and Expression of the Genes Encoding an Isocyclomaltooligosaccharide Glucanatransferase and an α-Amylase from a *Bacillus circulans* Strain," Biosci. Biotechnol. Biochem. 70 (11), 2690-2702 (2006).
International Search Report, PCT/GB2018/052937, dated Feb. 11, 2019.
Written Opinion, PCT/GB2018/052937, dated Feb. 11, 2019.
Ravagnani, Adriana, et al., "Spo0A directly controls the switch from acid to solvent production in solvent-forming clostridia", Molecular Microbiology, vol. 37, No. 5, Sep. 1, 2000, pp. 1172-1185.
Sandoval, Nicholas R. et al., "Whole-genome sequence of an evolved Clostridium pasteurianum strain reveals Spo (A deficiency responsible for increased butanol production and superior growth", Biotechnology for Biofuels, vol. 8, No. 1, Dec. 1, 2015.
Harris, L.M., et al., "Northern, morphological, and fermentation analysis of SpoOA inactivation ad overexpression in Clostridium acetobutylicum ATCC 824", Journal of Bacteriology, American Society for Microbiology, US, vol. 184, No. 13, Jul. 1, 2002.
Pajatsch et al., Pajatsch et al "The periplasmic cyclodextrin binding protein CymE from Klebsiella oxytoca and its role in maltodextrin and cyclodextrin transport" Journal of Bacteriology, 2630-2635 (1998).
UK Search Report, GB1716845.1, dated Jun. 28, 2018.
Kamionka et al., "Bacillus subtilis contains a cyclodextrin-binding protein which is part of a putative ABC-transporter" FEMS Microbiology Letters 204, 55-60 (2001).
Mora et al., "Partial purification and properties of cyclodextrin glycosyltransferase (CGTase) from alkalophilic Bacillus species" SpringerPlus 1:61 (2012).
Kitahata, Sumio et al., "Comparison of Action of Cyclodextrin Glucanotransferase from *Bacillus megaterium*, *B. circulans*, *B. stearothermophilus* and *B. macerans*", J. Jap. Soc. Starch Sci., 1982, vol. 29, No. 1, pp. 13-18.
Watanabe, Hikaru et al., "A Novel Glucanotransferase from a *Bacillus circulans* Strain That Produces a Cyclomaltopentaose Cyclized by an α-1, 6-Linkage", Biosci. Biotechnol. Biochem., 2006, vol. 70, Issue 8, pp. 1954-1960.

* cited by examiner

FIG. 6A

```
  1 MEDSKISVLI ADDNKEFCSI LNDYLLNQKD IVVTGIAKDG REALDLIVER KPDLVILDII
 61 MPHLDGLGVL EKLNTMNLEK VPRIIILSAV GQDKITQQAI TLGADYYTVK PFDMEVFTKR
121 IREMFNGAPA QESNVRASSY MQSPVMTSGE PKSKTPVDLE TEITNIIHEV GVPAHIKGYM
181 YLREAITMVV NDMELLSAVT KELYPSIAKK YNTTASRVER AIRHAIEVAW GRGQIDAINR
241 LFGYTVHTEK GKPTNSEFIA [I]IADKLRLKN KVS
```

FIG. 6B

```
  1 MEDSKISVLI ADDNKEFCSI LNDYLLNQKD IVVTGIAKDG REALDLIVER KPDLVILDII
 61 MPHLDGLGVL EKLNTMNLEK VPRIIILSAV GQDKITQQAI TLGADYYTVK PFDMEVFTKR
121 IREMFNGAPA QESNVRASSY MQSPVMTSGE PKSKTPVDLE TEITNIIHEV GVPAHIKGYM
181 YLREAITMVV NDMELLSAVT KELYPSIAKK YNTTASRVER AIRHAIEVAW GRGQIDAINR
241 LFGYTVHTEK GKPTNSEFIA [T]IADKLRLKN KVS
```

PROCESSES FOR PRODUCING ORGANIC SOLVENTS USING *CLOSTRIDIUM SACCHAROPERBUTYLACETONICUM*

FIELD

The present invention relates to a process for culturing *Clostridium saccharoperbutylacetonicum* cells which are capable of growing on gamma-cyclodextrin in a liquid culture medium in a culture vessel. The present invention also relates to a process for producing a bio-product, the process comprising culturing *Clostridium saccharoperbutylacetonicum* cells which are capable of growing on gamma-cyclodextrin in a liquid culture medium in a culture vessel. The invention also provides a process for reducing or eliminating growth of a contaminating bacterium in a culture medium which comprises *Clostridium saccharoperbutylacetonicum* cells, the process comprising culturing the *Clostridium saccharoperbutylacetonicum* cells in a culture medium comprising gamma-cyclodextrin. The invention also provides a system for use with the processes of the invention.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 32600324_1.txt, the date of creation of the ASCII text file is Apr. 9, 2020, and the size of the ASCII text file is 7.63 KB.

BACKGROUND

The butanol fermentation process utilises renewable bio-based feedstocks and is often referred to as the ABE fermentation after its major chemical products (i.e. acetone, butanol and ethanol). The ABE fermentation was first commercialised in the UK in 1916 and spread around the globe during the 1st and 2nd World Wars, mainly to produce acetone for munitions and butanol for paint lacquers. The process fell out of favour in the US and EU in the 1950s, when it struggled to compete with petro-derived equivalents on cost; but it persisted in China, Russia and South Africa until the 1980s. Today, due to higher oil prices, concerns over the supply of oil and environmental concerns over greenhouse gas (GHG) emission, the ABE fermentation process is being re-commercialised. The global n-butanol market, largely feeding into the paints, coatings, adhesives and inks sectors, is valued at greater than $6 billion (~3.7 million tonnes) and growing. Presently, bio-n-butanol production is only a small fraction of this, but the fermentation route has the potential to replace petro-derived butanol, acetone and hydrogen with cheaper, more sustainable and environmentally-friendly chemicals.

Traditional batch processes for the fermentation of starch to produce ABE have been practised for decades (e.g. Jones, D. T. and Woods, D. R. (1986) Microbiol. Rev. 50: 484-524). In such processes, starch is converted to glucose by enzyme treatment such as purified alpha-amylase and glucoamylase.

However, starch can also be converted into alternative substrates through the use of enzymes called cyclodextrin glucanotransferases (CGTases). These enzymes hydrolyse starch to cyclic products, i.e. cyclodextrins (CDs).

Cyclodextrins are cyclic glucose oligosaccharides which are generally composed of alpha-(1,4) linked glucopyranose subunits. Common cyclodextrins include alpha-cyclodextrin (6-membered sugar ring), beta-cyclodextrin (7-membered sugar ring) and gamma-cyclodextrin (8-membered sugar ring). Various less-commonly studied cyclodextrins are also known to be made by some species of bacteria, such as a 5-membered sugar ring with an alpha-(1,6) linkage (Watanabe, H. et al., Biosci. Biotechnol. Biochem. 70 (11), 2690-2702 (2006)), a 4-membered sugar ring (Mukai et al., Appl. Environ. Microbiol., 72(2), 1065-71 (2006)) and a variety of larger cyclodextrins with larger rings (Larsen, K., Journal of Inclusion Phenomena and Macrocyclic Chemistry, Volume 43 (2) (2004)).

Cyclodextrins are generally produced by the enzymatic conversion of starch using enzymes such as cyclodextrin glucanotransferases. Cyclodextrin glucanotransferases (CGTases) are also known as cyclodextrin glycosyl transferases and cyclodextrin glucosyltransferases. These enzymes are generally only found in bacteria, particularly bacteria of the genus *Bacillus* (e.g. *B. circulans*, *B. macerans* and *B. stearothermophilus*).

*Clostridium thermohydrosulfuricum* is no longer a valid species name (i.e. it is not on the LPSN List of Prokaryotic Names with Standing in Nomenclature [Parte, A. C. (2018). "LPSN—List of Prokaryotic names with Standing in Nomenclature (bacterio.net), 20 years on". International Journal of Systematic and Evolutionary Microbiology, 68, 1825-1829; doi: 10.1099/ijsem.0.002786]) and *Clostridium thermohydrosulfuricum* strains have now been reclassified as belonging to the *Thermoanaerobacter* genus (e.g. [Lee, Y.-E., et al. "Taxonomic Distinction of Saccharolytic Thermophilic Anaerobes: Description of *Thermoanaerobacterium xylanolyticum* gen. nov., sp. nov., and *Thermoanaerobacterium saccharolyticum* en. nov., sp. nov.; Reclassification of *Thermoanaerobium brockii*, *Clostridium thermosulfurogenes*, and *Clostridium thermohydrosulfuricum* E100-69 as *Thermoanaerobacter brockii* comb. nov., *Thermoanaerobacterium thermosulfurigenes* comb. nov., and *Thermoanaerobacter thermohydrosulfuricus* comb. nov., Respectively; and Transfer of *Clostridium thermohydrosulfuricum* 39E to *Thermoanaerobacter ethanolicus*." Int. J. Syst. Bacteriol., 43, 41-51. 1993.] and [Gregory M. Cook, Hush W. Morgan "Hyperbolic growth of *Thermoanaerobacter thermohydrosulfuricus* (*Clostridium thermohydrosulfuricum*) increases ethanol production in pH-controlled batch culture" Applied Microbiology and Biotechnology March 1994, Volume 41, Issue 1, pp 84-89.]).

Similarly, it has been proposed that *Clostridium thermoamylolyticum* should also be reclassified as *Thermoanaerobacter* due to its high sequence relatedness with *Thermoanaerobacter* species (Collins, M. D. et al. (1994). The phylogeny of the genus *Clostridium*: proposal of five new genera and eleven new species combinations. Int. J. Syst. Bacteriol., 44(4), 812-26).

The genus *Thermoanaerobacter* has now been clearly established by sequence analysis and shown that it forms a separate and distinct genus from *Clostridium sensu stricto* (Cluster I) (Stackebrandt et al. (1999) Phylogenetic basis for a taxonomic dissection of the genus *Clostridium*. FEMS Immunol. Med. Microbiol., 24(3), 253-8).

It is known that some bacteria will only grow on certain cyclodextrins. For example, it is reported that *B. subtilis* preferentially grows on β- and γ-cyclodextrins and only marginally on α-cyclodextrins, and that *K. oxytoca* will grow on α- and β-cyclodextrins but not on γ-cyclodextrin (Kamionka and Dahl, FEMS Microbiol. Letts. 204, 55-60 (2001)). Similarly, Marchini et al. (Arch. Microbiol. 164(4), p. 290 (1995)) report that *H. pylori* will grow on α- and β-cyclodextrins, but not on γ-cyclodextrin.

Furthermore, different types of CGTase can produce different types of cyclodextrin. WO2014/122449A1 discloses a CGTase enzyme from *C. saccharoperbutylacetonicum*. Based on sequence alignments and homology searches, the CGTase from WO2014/122449A1 is stated to be different to the well-characterised alpha-, beta- and gamma-CGTases. For example, protein alignments show that it clusters with CGTases from *B. circulans* and *Arthrobacter* which do not form the standard alpha-, beta- or gamma-cyclodextrins containing 6, 7 or 8 glucose units with α1-4 linkages. The CGTase from WO2014/122449A1 is therefore not expected to convert starch through the well-characterised alpha-, beta- or gamma-cyclodextrin routes; instead, it appears to cyclise starch using a different mechanism. There is no indication therefore in WO2014/122449A1 that Clostridia are capable of utilising alpha-, beta- or gamma-cyclodextrins as a carbon source.

Cyclodextrins have a cone-like structure. The internal cavity surface is more hydrophobic than the external surface of the molecule. As a result, cyclodextrins are able to form inclusion complexes with hydrophobic (guest) molecules. The resulting complexes are generally more water-soluble than the non-complexed hydrophobic molecule.

Cyclodextrins have many uses in industry, including in separation and extraction processes, as drug-delivery agents and as stabilisers in the food industry. Cyclodextrins have also been used as intermediates in the production of ethanol (e.g. WO1989/003421).

In industrial fermentation processes, it is desired to grow a defined bacterial culture in the fermentation vessel. However, there is a constant risk of contamination of this defined culture with other strains that may be present in the local environment or may be brought in with the feedstock or other consumables. In the industrial production of commodity chemicals, it is often not commercially viable to build and run a completely sterile process. A historical review of industrial ABE fermentation of starches, using *Clostridium* spp. [Beesch, 1953, Acetone-butanol fermentation of starches. Appl. Microbiol., 1(2), 85-95] states that: "The greatest problem in the fermentation industry is maintenance of sterile conditions . . . . The lactic acid bacteria are the most common contaminants".

SUMMARY

It has now been found that the *Clostridium* species *C. saccharoperbutylacetonicum* is capable of utilising gamma-cyclodextrin (but not alpha-cyclodextrin) as a fermentable carbohydrate source. Furthermore, growth on gamma-cyclodextrin results in improved bio-product titres compared to growth on glucose. This phenomenon is not seen when other common cyclodextrins (e.g. alpha- or beta-cyclodextrin) are used as the main carbohydrate source. This unexpected finding opens up the possibility of obtaining bio-products from certain *Clostridium* species using new substrates which may provide higher yields.

Additionally, since few other bacteria (including some other *Clostridium* species) are capable of utilising gamma-cyclodextrin as a carbon source, this discovery allows for processes to produce bio-products using *Clostridium saccharoperbutylacetonicum* which are less susceptible than previous fermentation processes to contamination from other bacteria, such as lactic acid bacteria and *Clostridium tyrobutyricum*.

This discovery also provides a new process of reducing or eliminating contamination of bio-product-producing processes which use certain *Clostridium saccharoperbutylacetonicum* strains by switching—temporarily or permanently—to the use of a gamma-cyclodextrin-based carbon source in order to eliminate growth of the contaminating bacteria.

The discovery that *C. saccharoperbutylacetonicum* is able to effectively utilise gamma-cyclodextrin as a carbon source was made and studied using wild-type *C. saccharoperbutylacetonicum* (as described herein in Examples 1, 2, 3, 4 and 7).

Whilst wild-type *C. saccharoperbutylacetonicum* does not readily sporulate on glucose-based media under normal growth conditions (typically no spores would be seen at 72 hours—see Example 10 herein), it has now surprisingly been found that cultures of the wild-type *C. saccharoperbutylacetonicum* sporulate much more readily on gamma-cyclodextrin, with spores seen in cultures as young as 20 hours. (In processes for the production of bio-products such as those disclosed herein, early sporulation is undesirable because the cells become dormant and hence cease production of the bio-product.)

It has now been found, however, that sporulation can be delayed by making use of a sporulation-deficient *Clostridium saccharoperbutylacetonicum* mutant in the processes of the invention. In such a way, longer bio-product production times can be achieved. The use of such sporulation-deficient *Clostridium saccharoperbutylacetonicum* mutants in the processes disclosed herein relates to a particularly preferred embodiment of the invention.

It is therefore one object of the invention to provide a process which facilitates one or more of the above-mentioned features. The invention also provides a system for use with such a process.

In one embodiment, the invention provides a process for culturing *Clostridium saccharoperbutylacetonicum* cells, the process comprising the step:
  (a) culturing *Clostridium saccharoperbutylacetonicum* cells in a liquid culture medium in a culture vessel, wherein the *Clostridium saccharoperbutylacetonicum* cells are ones which are capable of utilising gamma-cyclodextrin as a carbon source, and wherein the culture medium comprises or is being fed gamma-cyclodextrin as a carbon source and optionally one or more other carbon sources.

In a further embodiment, the invention provides a process for producing a bio-product, the process comprising the steps:
  (a) culturing *Clostridium saccharoperbutylacetonicum* cells in a liquid culture medium in a culture vessel, wherein the *Clostridium saccharoperbutylacetonicum* cells are ones which are capable of producing the bio-product, wherein the *Clostridium saccharoperbutylacetonicum* cells are ones which are capable of utilising gamma-cyclodextrin as a carbon source, and wherein the culture medium comprises or is being fed gamma-cyclodextrin as a carbon source and optionally one or more other carbon sources; and optionally
  (b) harvesting and/or purifying one or more bio-products from the *Clostridium saccharoperbutylacetonicum* cells or from the culture medium.

The invention also provides a system for the production of a bio-product, the system comprising:
  (i) a culture vessel comprising *Clostridium saccharoperbutylacetonicum* cells in a liquid culture medium; and optionally
  (ii) monitoring apparatus for monitoring growth of cells in the culture vessel;

wherein the *Clostridium saccharoperbutylacetonicum* cells are ones which are capable of producing the bio-product, wherein the *Clostridium saccharoperbutylacetonicum* cells are ones which are capable of utilising gamma-cyclodextrin as a carbon source, and wherein the liquid culture medium comprises or is being fed gamma-cyclodextrin as a carbon source, and optionally one or more other carbon sources.

The system is preferably adapted to carry out a process of the invention.

The invention further provides a process for reducing or eliminating growth of a contaminating bacterium in a culture medium comprising *Clostridium saccharoperbutylacetonicum* cells, the process comprising the steps:
  (a) culturing *Clostridium saccharoperbutylacetonicum* cells in a liquid culture medium in a culture vessel, wherein the culture medium comprises one or more carbon sources but does not comprise gamma-cyclodextrin, wherein the *Clostridium saccharoperbutylacetonicum* cells are ones which are capable of utilising gamma-cyclodextrin as a carbon source, wherein the culture medium comprises sufficient carbon sources to support growth of the *Clostridium saccharoperbutylacetonicum* cells, wherein the culture vessel additionally comprises a contaminating bacterium which is not capable of utilising gamma-cyclodextrin as a carbon source; and
  (b) increasing the concentration of gamma-cyclodextrin in the culture medium and reducing the concentration of at least one of the said other carbon sources in the culture medium to concentrations wherein the growth of the *Clostridium saccharoperbutylacetonicum* cells is favoured over the growth of the contaminating bacterium;
thereby reducing or eliminating growth of the contaminating bacterium in the culture vessel.

In yet another embodiment, the invention provides a process for reducing or eliminating growth of a contaminating bacterium in a culture medium comprising *Clostridium saccharoperbutylacetonicum* cells, the process comprising the steps:
  (a) culturing *Clostridium saccharoperbutylacetonicum* cells in a liquid culture medium in a culture vessel, wherein the *Clostridium saccharoperbutylacetonicum* cells are ones which are capable of utilising gamma-cyclodextrin as a carbon source, wherein the culture medium comprises gamma-cyclodextrin as a carbon source and additionally one or more other carbon sources, wherein the culture medium comprises sufficient carbon sources to support growth of the *Clostridium saccharoperbutylacetonicum* cells, wherein the culture vessel additionally comprises a contaminating bacterium which is not capable of utilising gamma-cyclodextrin as a carbon source; and
  (b) reducing the concentration of at least one of the said other carbon sources in the culture medium to a concentration wherein the growth of the *Clostridium saccharoperbutylacetonicum* cells is favoured over the growth of the contaminating bacterium;
thereby reducing or eliminating growth of the contaminating bacterium in the culture vessel.

The process of the invention may be operated in any suitable manner. For example, it may be operated as a batch process, fed-batch process or any form of continuous process or perfusion process; or a mixture of these types of processes.

In some embodiments, the process is operated in fed-batch mode. In this embodiment, the micro-organism is cultured under desired growth conditions in a batch mode for a suitable time, e.g. about 20 hours until approximately half the sugars or sugar precursors (e.g. cyclodextrins) are consumed (e.g. 5-30 g/L). When using monophasic solventogenic *Clostridium saccharoperbutylacetonicum*, the *Clostridium saccharoperbutylacetonicum* cells multiply and produce both acids and solvents (or alternative bio-products, e.g. in cases where the *Clostridium saccharoperbutylacetonicum* cells have been engineered to generate these). The initial volume of the first batch stage of the process should preferably be about 65% (e.g. 40%-90%) of the total working volume in the vessel and contain enough sugar or sugar precursor (e.g. 10-50 g/L) and nutrients to sustain growth and good bio-product yields (e.g. greater than 0.3 g solvents/g sugar or sugar precursor). The fermenter is fed with a concentrated sugar or sugar precursor solution and nutrients in a volume that equates to about 30% (e.g. 25%-35%) of the culture vessel's working capacity and is fed at a rate designed to last for a finite number of hours (e.g. between 10-200 hours). In situ product removal may result in removal of material during the process. Therefore, the total added volume can be greater than the tank volume. The optimal volumes may be adjusted depending on progress of the individual fermentations. The *Clostridium saccharoperbutylacetonicum* cells are maintained under conditions that are suitable for them to grow optimally (e.g. temperature, pH, redox, etc.) and to produce bio-products, e.g. solvents.

The process of the invention is preferably operated under continuous culture conditions. As used herein, the term "continuous culture conditions" refers to a process wherein the culture of *Clostridium saccharoperbutylacetonicum* cells in the culture vessel is capable of being maintained with a continuous or substantially continuous flow of feed (nutrients) in steady-state conditions (defined by high sugar (or sugar precursor) uptake rates and bio-product productivity) for prolonged periods of time (e.g. >75 hours). Under this scenario, some bleed may be required to maintain a constant volume in the culture vessel.

BRIEF DESCRIPTION OF THE DRAWINGS

FIG. 6A: Amino acid sequence of wildtype Spo0A (SEQ ID NO: 1). Residue 1261 is indicated with a box. FIG. 6B: Amino acid sequence of I261T Spo0A (SEQ ID NO: 2). Residue 261 (T), is indicated with a box.

DETAILED DESCRIPTION

Figure 1A:
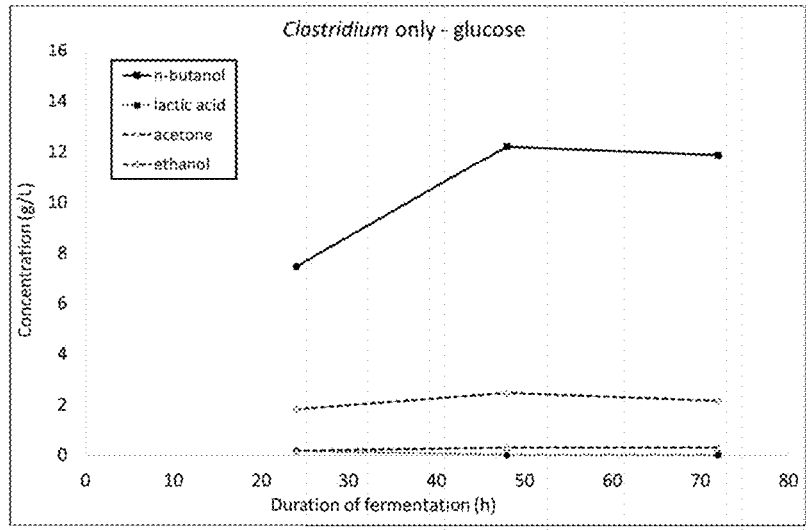
FIGS. 1A-1F show the growth of *Clostridium* and *Lactobacillus* on glucose or gamma-cyclodextrin.
Figure 1B:
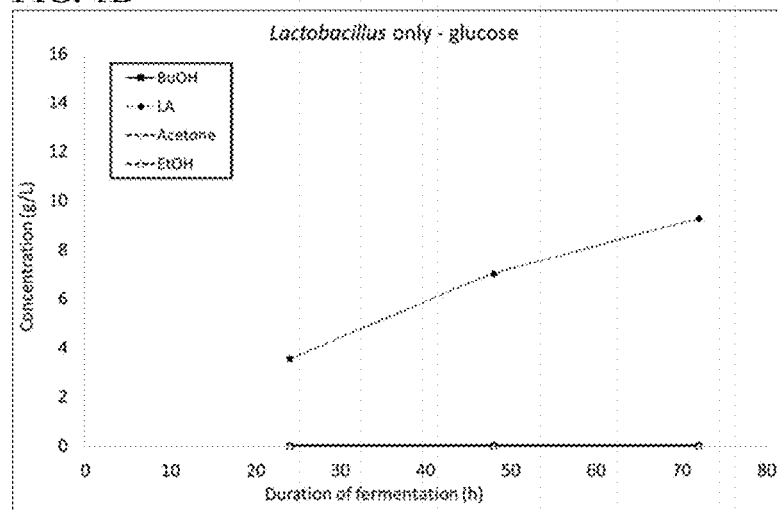
Figure 1C:
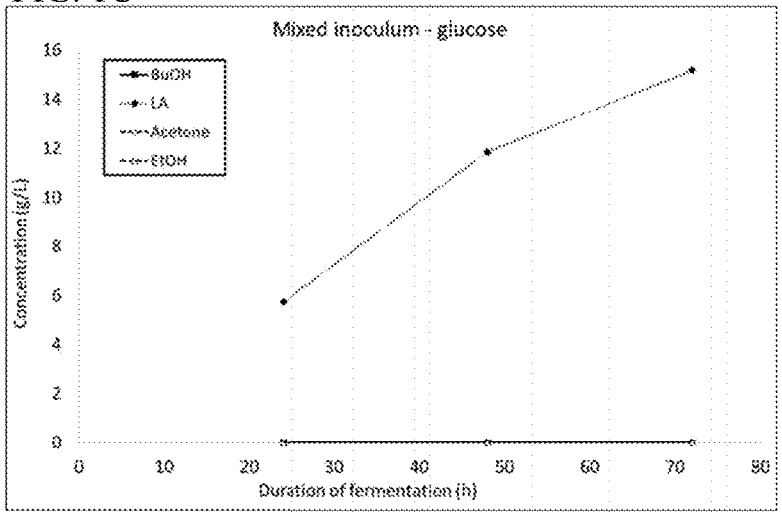
Figure 1D:
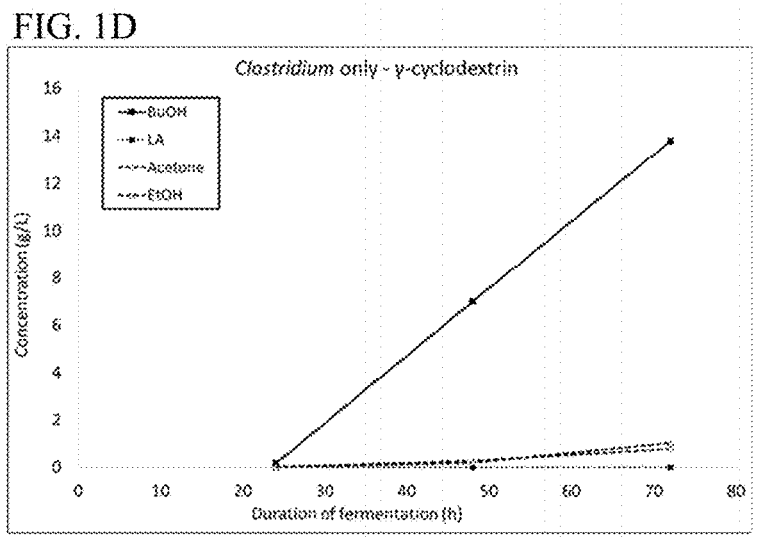
Figure 1E:
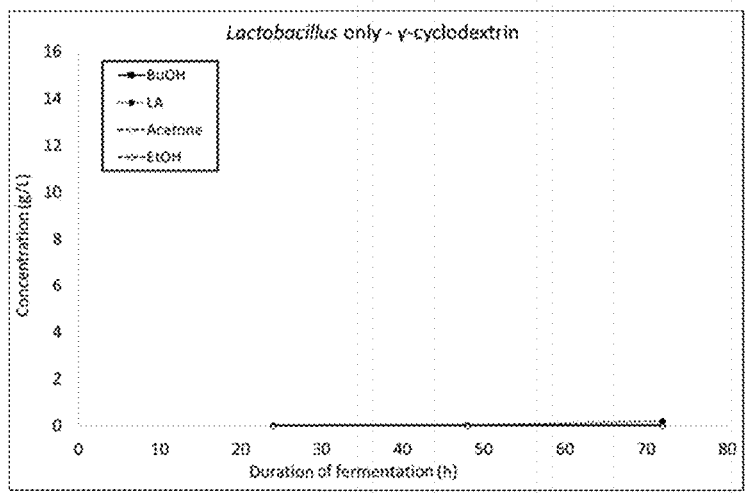
Figure 1F:
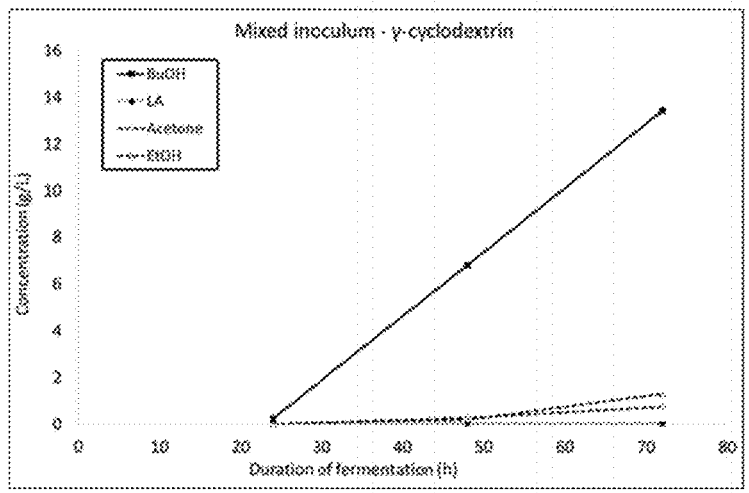

As used herein, the term "bio-product" refers to products which are capable of being produced by *Clostridium saccharoperbutylacetonicum* either using endogenous metabolic pathways, or resulting from synthetic biology or genetic engineering of the *Clostridium saccharoperbutylacetonicum*.

Preferably, the bio-product is a solvent, more preferably an organic solvent, most preferably n-butanol, ethanol and/or acetone.

The processes of the invention relate to culturing *Clostridium saccharoperbutylacetonicum* cells. The *Clostridium saccharoperbutylacetonicum* cells are from a strain of *Clostridium saccharoperbutylacetonicum* or a variant or derivative thereof.

In some preferred embodiments, the *Clostridium saccharoperbutylacetonicum* is a solventogenic *Clostridium saccharoperbutylacetonicum*. Solventogenic *Clostridium saccharoperbutylacetonicum* are bacteria that are capable of producing solvents, such as acetone, butanol and/or ethanol, preferably acetone, butanol and ethanol.

The term "acid-producing" or "acidogenic" as used herein refers to the ability of a *Clostridium* to convert a substrate based on cyclodextrins, sugars and/or starches into RCOOH (wherein R is as defined below), for example into acetate and/or butyrate.

The term "solvent-producing" or "solventogenic" refers to the ability of a *Clostridium saccharoperbutylacetonicum* to convert a substrate based on sugars and/or starches into a solvent, preferably into one or more of acetone, ethanol and/or butanol.

As used herein, the term "solvent" or "solvents" refers to low boiling point organic solvents or their azeotropes which are capable of being produced by solventogenic *Clostridium saccharoperbutylacetonicum* in a liquid fermentation medium. Examples of such solvents include alcohols of formula R—OH, wherein R is an aliphatic $C_1$-$C_8$ alkyl group or an aliphatic $C_2$-$C_8$ alkenyl group. The R group may be branched or linear. Preferably, it is linear. The R group may be saturated or unsaturated. Preferably it is saturated. Other examples of solvents include acetone.

Preferred examples of alcohols of formula R—OH include methanol, ethanol, propan-1-ol, 2-methyl-propan-1-ol, propan-2-ol, 2-methyl propan-2-ol, 1,3-propanediol, 1-butanol, 2-butanol, pentanol, hexanol, heptanol and octanol. A further example of a solvent has a formula R—CO including acetone (($CH_3$)$_2$CO).

Preferably, the solvents comprise ABE solvents, i.e. acetone, 1-butanol and ethanol. Most preferably, the solvents comprise 1-butanol or substantially 1-butanol.

The *Clostridium saccharoperbutylacetonicum* may be biphasic or monophasic. In a biphasic fermentation, acids are typically produced first and then re-assimilated into solvents. In most solventogenic *Clostridium saccharoperbutylacetonicum*, fermentation is biphasic: the first phase is characterised by cell growth, acid production and a fall in culture pH; in the second phase, the acids are converted to solvents and the culture pH increases. The switch in metabolism is triggered by the acid concentration in the fermentation broth and/or low culture pH values.

Preferably, the *Clostridium saccharoperbutylacetonicum* is a monophasic *Clostridium saccharoperbutylacetonicum*. As used herein, the term "monophasic *Clostridium saccharoperbutylacetonicum*" means that the *Clostridium saccharoperbutylacetonicum* do not have distinct acid- and solvent-producing phases. Monophasic solvent production is characterised by simultaneous growth and solvent production; and with no obvious switch or change in metabolism. Acids do not tend to accumulate in the culture media.

The *Clostridium saccharoperbutylacetonicum* are ones which are capable of utilising gamma-cyclodextrin as a sugar source or a carbon source.

The *Clostridium saccharoperbutylacetonicum* which are used in the process of the invention are ones which are capable of catabolising gamma-cyclodextrin, i.e. they can break down gamma-cyclodextrin into molecules that can enter into central metabolic pathways leading to generation of ATP (e.g. the Embden-Meyerhof-Parnas pathway (also called the EMP pathway or glycolysis), the pentose-phosphate pathway or the Entner-Doudoroff pathway). The generation of pathway-entry molecules from gamma-cyclodextrin optionally occurs via the formation of glucose-based oligosaccharide and/or disaccharide intermediates, and optionally involves phosphorylation.

In some embodiments, the *Clostridium saccharoperbutylacetonicum* are ones which are capable of breaking down gamma-cyclodextrin to glucose monomers or glucose-based disaccharides or glucose-based oligosaccharides e.g. linear or cyclic dextrins.

Preferably, the *Clostridium saccharoperbutylacetonicum* is a N1-strain or a variant or derivative thereof. Even more preferably, the *Clostridium saccharoperbutylacetonicum* is *Clostridium saccharoperbutylacetonicum* N1-4(HMT) or N1-504, or a variant or derivative thereof.

*C. saccharoperbutylacetonicum* strain N1-4(HMT) may be obtained from ATCC deposit number 27021 or from other culture collections, e.g. National Collection of Industrial, Food and Marine Bacteria, UK (NCIB), deposit number 12606 or German Collection of Microorganisms and Cell Cultures (DSM) deposit number 14923. *C. saccharoperbutylacetonicum* strain N1-504 may be obtained from ATCC deposit number 27022, or DSM No. 2152 or NCIB 12605. Both of these strains are monophasic.

In some preferred embodiments, the *Clostridium saccharoperbutylacetonicum* is:

(i) *Clostridium saccharoperbutylacetonicum* N1-4(HMT) or N1-504, or (ii) as deposited under ATCC 27021 or ATCC 27022 (or another of the deposits mentioned above), or a monophasic and solventogenic variant or derivative thereof.

In some embodiments of the invention, the *Clostridium saccharoperbutylacetonicum* is not *C. saccharoperbutylacetonicum* strain N1-4. *C. saccharoperbutylacetonicum* strain N1-4 was previously available as ATCC deposit number 13564. This deposit is, however, no longer available from the ATCC.

Preferably, the variant or derivative has one or more or all of the following properties:

(i) it is capable of utilising gamma-cyclodextrin as a sugar source or a carbon source;

(ii) it is capable of producing one or more or all of acetone, butanol or ethanol, preferably at least butanol;

(iii) it is a monophasic solventogenic *Clostridium saccharoperbutylacetonicum*; and/or (iv) it produces the same or more acetone, ethanol and/or butanol compared to the parent *Clostridium saccharoperbutylacetonicum* (e.g. as deposited in ATCC 27021 or ATCC 27022) of which it is a variant or from which it is derived, under equivalent conditions.

In other embodiments, the *Clostridium saccharoperbutylacetonicum* is a variant or derivative of *Clostridium saccharoperbutylacetonicum* N1-4(HMT) or N1-504, wherein the mutant or derivative is capable of utilising gamma-cyclodextrin as a sugar source or a carbon source, optionally wherein it has been engineered to produce an alternative bio-product compared to the parent *Clostridium saccharoperbutylacetonicum* of which it is a variant or from which it is derived, under equivalent conditions.

Such variants/derivatives may produce more of the alternative bio-product(s) (compared to the parent *Clostridium saccharoperbutylacetonicum* of which it is a variant or from which it is derived, under equivalent conditions); this may mean that they produce less acetone, ethanol and/or butanol compared to the *Clostridium saccharoperbutylacetonicum* of which it is a variant or from which it is derived (as the metabolism of the *Clostridium saccharoperbutylacetonicum* is directed along alternative pathway(s)).

In some embodiments, the *Clostridium saccharoperbutylacetonicum* is a variant or derivative of *Clostridium saccharoperbutylacetonicum* N1-4(HMT) or N1-504, wherein the variant or derivative has been adapted to utilise gamma-cyclodextrin more efficiently than the parental strain as a sugar source or a carbon source. This could include selecting for a derivative whose lag period (between first contact with gamma-cyclodextrin and subsequent ability to rapidly metabolise gamma-cyclodextrin) has been reduced, e.g. using adaptive evolution selecting for fast growers on gamma-cyclodextrin. It could include a strain that has been adapted (including evolved) to constitutively express and/or have permanently active proteins for utilisation of gamma-cyclodextrin. It could also include a strain where this phenotype (enhanced utilisation of gamma-cyclodextrin) has been engineered.

In some embodiments, a *Clostridium saccharoperbutylacetonicum* strain which was not originally able to utilise gamma-cyclodextrin has been engineered to be able to utilise gamma cyclodextrin, by taking part or all of the pathway responsible for this function in *C. saccharoperbutylacetonicum* strains N1-4 (HMT), or from N1-504, and incorporating into a *Clostridium* that does not normally have this pathway.

Such variants and derivatives may be produced, for example, by random mutagenesis and adaptive evolution or by recombinant methods. Recombinant methods include insertional inactivation of genes through use of Type II introns, e.g. Targetron (Sigma) and Clostron (e.g. WO 2007/148091), integration of new genes through use of 'allele coupled exchange' (ACE, e.g. WO 2009/101400), and genome editing techniques—based on CRISPR (e.g. WO 2015/159087; and Wang et al. (2016) Bacterial Genome Editing with CRISPR-Cas9: Deletion, Integration, Single Nucleotide Modification, and Desirable "Clean" Mutant Selection in *Clostridium beijerinckii* as an Example. ACS Synth Biol. 2016 Apr. 26. [Epub ahead of print]. Recombinant methods can be used to change the product profile of *Clostridium*, for example, a plasmid carrying the adh gene caused *C. acetobutylicum* ATCC 824 to produce 2,3-butanediol (Collas et al. (2012) Simultaneous production of isopropanol, butanol, ethanol and 2,3-butanediol by *C. acetobutylicum* ATCC 824 engineered strains. AMB Express, 2(1) 45). Random mutagenesis techniques could also be used, as previously demonstrated for generating a more acetate-tolerant strain (Yang, S. et al. (2010). Paradigm for industrial strain improvement identifies sodium acetate tolerance loci in *Zymomonas mobilis* and *Saccharomyces cerevisiae*. Proc Natl Acad Sci USA., 107(23), 10395-400), for generating a more ethanol-tolerant strain (Shao, X., et al. (2011). Mutant selection and phenotypic and genetic characterization of ethanol-tolerant strains of *Clostridium thermocellum*. Appl Microbiol Biotechnol. 92(3), 641-52. 2011. Also: Brown, S. D., et al. (2011). Mutant alcohol dehydrogenase leads to improved ethanol tolerance in *Clostridium thermocellum*. Proc Natl Acad Sci USA., 108(33), 13752-7) and for generating a more amylolytic strain (Annous, B. A., & Blaschek, H. P. (1991). Isolation and characterization of *Clostridium acetobutylicum* mutants with enhanced amylolytic activity. Appl. Environ. Microbiol., 57(9), 2544-8.)

Such variants and derivatives may be tested by screening them in small-scale fermentations, i.e. looking for variants or derivatives that retain/gain ability to grow on gamma-cyclodextrin and produce the same or more of the target bio-product (e.g. acetone, ethanol and/or butanol) compared to the *Clostridium saccharoperbutylacetonicum* from which it is derived, under equivalent conditions.

In some embodiments, the defined bacterial culture comprises more than one *Clostridium saccharoperbutylacetonicum* strain, each of which is capable of utilising gamma-cyclodextrin as a sugar source or a carbon source, and is capable of producing one or more of the target bio-product(s), for example, but not necessarily, acetone, butanol or ethanol, preferably at least butanol.

In some embodiments, the *Clostridium saccharoperbutylacetonicum* which are used in the culture vessel are from a single strain.

The *Clostridium saccharoperbutylacetonicum* cells which are used in the processes of the invention are preferably a defined bacterial culture. A defined bacterial culture is an aseptically-prepared inoculum containing the specific bacteria involved in making the target bio-product. It could be a single pure strain (e.g. *C. saccharoperbutylacetonicum* N1-4 (HMT), or *C. saccharoperbutylacetonicum* N1-504 and single strain derivatives thereof), or it could be a mixture of closely-related strains (e.g. generated from a single strain during adaptive evolution). Alternatively, it could be a mixture of species that together efficiently generate a target product, e.g. an acetogen combined with a solventogen, which perform complementary parts of a product formation pathway (e.g. U.S. Pat. No. 5,753,474 which describes the use of two *Clostridium* strains, with *C. thermobutyricum* (producing butyric acid) in the first stage vessel linked to a second stage vessel with *C. acetobutylicum* (converting butyric acid to butanol).)

It has now been found that cultures of the wild-type *C. saccharoperbutylacetonicum* sporulate much more readily when grown on gamma-cyclodextrin compared to when they are grown on glucose, with spores seen in cultures as young as 20 hours (see Example 10 herein). Sporulation at such an early time is undesirable (although workable) because it limits the duration of the bio-product-producing (e.g. solvent-producing) time.

It has now been found that *C. saccharoperbutylacetonicum* derivatives which are sporulation-deficient are capable of maintaining their capacity to produce solvents, as compared to non-sporulation deficient strains.

In a particularly preferred embodiment of the invention, therefore, the *Clostridium saccharoperbutylacetonicum* is a sporulation-deficient *C. saccharoperbutylacetonicum*.

There are numerous published examples of solventogenic *Clostridium* that are deficient in sporulation (e.g. asporogenic) whilst still being capable of producing solvents (solventogenic).

Examples of the production of sporulation-deficient *Clostridium* include the following:

The "spo-1" and "spo-2" derivatives of *Clostridium saccharobutylicum* NCP 262 are unable to form mature endospores (necessary for sporulation) yet produce normal levels of solvents. They were generated from wildtype *C. saccharobutylicum* NCP 262 using the chemical mutagen ethyl methanesulfonate (EMS) followed by selection on rifampin plates. (Jones, D. T., van der Westhuizen, A., Long, S., Allcock, E. R., Reid, S. J., & Woods, D. R. (1982) "Solvent Production and Morphological Changes in *Clostridium acetobutylicum*". Appl. Environ. Microbiol., 43(6), 1434-1439.)

Asporogenic solventogenic ATCC 39236 was derived from *Clostridium acetobutylicum* ATCC 4259 through continuous culture. (Lemme & Frankiewicz, U.S. Pat. No. 4,521,516 (1985), "Strain of *Clostridium acetobutylicum* and process for its preparation".)

Asporogenic solventogenic ATCC 55025 was derived from *C. acetobutylicum* ATCC 4259 using EMS (Jain, Beacom & Datta, U.S. Pat. No. 5,192,673, (1993) "Mutant strain of *C. acetobutylicum* and process for making butanol".)

A sporulation-inhibited solventogenic derivative of *C. acetobutylicum* ATCC 824 was produced by targeting antisense RNA to part of the SpoIIE gene. (Bennett & Scotcher (2008) U.S. Pat. No. 8,084,243 "Blocking sporulation by inhibiting spoIIE"), (Scotcher, M. C. & Bennett, G. N. (2005). "SpoIIE Regulates Sporulation but Does Not Directly Affect Solventogenesis in *Clostridium acetobutylicum* ATCC 824". Journal of Bacteriology 187, 1930-1936).

Another group independently knocked out the SpoIIE gene in *C. acetobutylicum* to generate an asporogenous solventogenic derivative. (Hess, Papoutsakis & Tracy, WO2011090985 (2011) "*Clostridium* cell in which expression of the SpoIIE gene of the *Clostridium* cell is silenced useful for industrial-scale production of chemical product such as butanol butyric acid (DWPI title)"), (Bi, C., Jones, S. W., Hess, D. R., Tracy, B. P. & Papoutsakis, E. T. (2011). "SpoIIE Is Necessary for Asymmetric Division, Sporulation, and Expression of σF, σE, and σG but Does Not Control Solvent Production in *Clostridium acetobutylicum* ATCC 824". Journal of Bacteriology 193, 5130-5137).

The hyper-solventogenic BA101 derivative of *Clostridium beijerinckii* NCIMB 8052 (initially deposited as *C. acetobutylicum*) was generated using the chemical mutagen N-methyl-N'-nitro-N-nitrosoguanidine together with selective enrichment on 2-deoxyglucose. (Annous & Blaschek (1991) "Isolation and characterization of *Clostridium acetobutylicum* mutants with enhanced amylolytic activity." Appl. Environ. Microbiol., 57(9), 2544-8). The BA101 derivative was shown to be "less efficient in sporulation" and "Maximal levels of induction of sporulation genes in *C. beijerinckii* BA101 were significantly lower than those in *C. beijerinckii* 8052, consistent with the observed lower level of endospore formation." (Shi & Blaschek (2008) "Transcriptional analysis of *Clostridium beijerinckii* NCIMB 8052 and the hyper-butanol-producing mutant BA101 during the shift from acidogenesis to solventogenesis". Appl. Environ. Microbiol., 74(24), 7709-7714.) This could involve "decreased expression of a [sporulation] gene selected from the group consisting of SpoIVA, SpoVB, and SspA" (Blaschek, Stoddard & Shi (2008) WO2008144060A2 "Methods and compositions for producing solvents").

An asporogenous mutant with improved butanol production (91% higher titre), M150B, was evolved from wild-type *C. pasteurianum* (ATCC 6013) using chemical mutagenesis and selective pressure. Sequence analysis revealed a deletion of 24 bp in M150B's spo0A gene resulting in an in-frame deletion of eight amino acid residues in the σA activator region essential for binding to σA-dependent promoters. (Sandoval, N. R., Venkataramanan, K. P., Groth, T. S., & Papoutsakis, E. T. "Whole-genome sequence of an evolved *Clostridium pasteurianum* strain reveals Spo0A deficiency responsible for increased butanol production and superior growth". Biotechnol Biofuels. 2015 Dec. 24; 8:227. doi: 10.1186/s13068-015-0408-7. eCollection 2015.) The authors also point out that mutations of *B. subtilis'* spo0A in this region have similarly been shown to have lower or failed activation from σA promoters and these mutants are also asporogenous.

A sigF gene knock-out in *Clostridium acetobutylicum* ATCC 824 disrupted the expression of the σ$^F$ sigma factor, which also had a knock-on effect on the expression of sigma factors σ$^E$, and σ$^G$. The sigF mutant (FKO1) failed to differentiate into spores prior to the asymmetric division, while still maintaining solvent production comparable to its parent strain so long as the inoculum was prepared at exponential or early stationary phase. (Jones, S. W., Tracy, B. P., Gaida, S. M. & Papoutsakis, E. T. (2011) "Inactivation of in *Clostridium acetobutylicum* ATCC 824 Blocks Sporulation Prior to Asymmetric Division and Abolishes σ$^E$ and σ$^G$ Protein Expression but Does Not Block Solvent Formation". Journal of Bacteriology, 193, 2429-2440.) The same group also created sigE and sigG knockouts to disrupt the expression of sigma factors σ$^E$ (EKO1 mutant) and σ$^G$ (GKO1 mutant). These mutants behaved similarly to the FKO1 mutant (Tracy, B. P., Jones, S. W. & Papoutsakis, E. T. (2011). "Inactivation of σ$^E$ and σ$^G$ in *Clostridium acetobutylicum* Illuminates Their Roles in Clostridial-Cell-Form Biogenesis, Granulose Synthesis, Solventogenesis, and Spore Morphogenesis". *Journal of Bacteriology* 193, 1414-1426).

The sporulation status of a population of *Clostridium* cells may be determined by phase-contrast microscopy. At the end of exponential growth, cells accumulate granulose and vegetal cells convert to swollen, bright-phase *Clostridium* forms and synthesize a capsule. The presence of a phase-bright forespore at the terminus of the cell (see FIG. 8) is considered to indicate that the cell is sporulating. The skilled artisan will also be aware of the appearance of later stages of sporulation (e.g. phase-bright mature endospores); these also count as sporulation. Events typically seen before forespore formation, such as granulose accumulation (e.g. FIG. 2F of Jones et al. (1982) Appl. Environ. Microbiol. 43(6), 1434-1439), do not, for the purpose of this invention, indicate that a cell is sporulating.

Once conditions that will result in sporulation and solventogenesis by the "endospore-forming" parent strain have been chosen, determination of a "sporulation-deficient" strain can be made by direct comparison with this. The specific conditions required to promote sporulation will depend on the parent strain. An example of conditions that have been successfully used is given in Example 10.

One suitable procedure is as follows:

(i) Grow prospective sporulation-deficient strain and appropriate control strain overnight.

(ii) Use the overnight cultures to inoculate small (e.g. 60 ml) fresh cultures on sporulation-compatible medium, in duplicate, at comparable starting cell densities.

(iii) Incubate the fresh cultures under appropriate conditions for solvent production and sporulation, and perform all subsequent steps on all replicates.

(iv) Aseptically remove small (e.g. 1 ml) samples every 24 hours, or more frequently. (A to sample is advisable to ensure that there are no fore/endospores carried over from the inoculum, and the time of the first sample is ideally based on predicted sporulation timings determined in preliminary experiments.)

(v) Assess the sporulation status of the culture in each sample using phase-contrast microscopy: Examine at least 20 microscope fields, on average having at least 50 cells in each field. Look for the presence of phase-bright forespores and endospores, and note if any are present. (The skilled artisan will be able to see if cultures are too dense for reliable assessment, and will be able to dilute the culture appropriately.)

(vi) Compare the results from the prospective sporulation-deficient strain with the results from the parent or wild type control strain.

(vii) To be designated as being "sporulation deficient", a mutant strain will have no visible fore/endospores at the time point when sporulation is first detected in the control strain, and will continue to have no visible fore/endospores in samples taken up to 24 hours later.

As used herein, the term "sporulation-deficient" encompasses *Clostridium saccharoperbutylacetonicum* which are asporogenic (also known as asporogenous), sporulation-incompetent and sporulation-impaired. It includes *Clostridium saccharoperbutylacetonicum* whose spores are not formed because the *Clostridium saccharoperbutylacetonicum* is not capable of forming spores; *Clostridium saccharoperbutylacetonicum* which have a diminished capability of forming spores; and *Clostridium saccharoperbutylacetonicum* wherein spores are formed, but the spores are not viable. The term "sporulation-deficient" also encompasses *Clostridium saccharoperbutylacetonicum* whose ability to sporulate is reduced and/or whose ability to sporulate is delayed.

As used herein, the term "ability to sporulate is reduced" means that the number of sporulation-deficient *Clostridium saccharoperbutylacetonicum* which are sporulating is lower (e.g. at least 2%, 5%, 10%, 20%, 50%, 100% or 200% lower) when compared to a wild-type *Clostridium* of the same species under equivalent conditions at a defined point in time when sporulation would normally be expected to occur.

As used herein, the term "ability to sporulate is delayed" means that the point in which sporulation is initiated is delayed (e.g. by at least 1, 2, 3, 4, 5, 10 or 24 hours) in the sporulation-deficient *Clostridium saccharoperbutylacetonicum* when compared to a wild-type *Clostridium saccharoperbutylacetonicum* of the same strain (e.g. as deposited in ATCC 27021 or ATCC 27022) under equivalent conditions at a defined point in time when sporulation would normally be expected to occur.

The initiation of sporulation may be defined as the point in which at least 10% of a random sample from the *Clostridium saccharoperbutylacetonicum* from the population of *Clostridium saccharoperbutylacetonicum* have a bright forespore when observed under phase-contrast microscopy.

In some embodiments, the *Clostridium saccharoperbutylacetonicum* may be sporulation-deficient when compared to a wild-type strain of the same species or the type strain for that species.

In other embodiments, the *Clostridium saccharoperbutylacetonicum* may be sporulation-deficient when compared to wild-type *C. saccharoperbutylacetonicum* N1-4(HMT) (ATCC 27021) or *C. saccharoperbutylacetonicum* N1-504 (ATCC 27022) under controlled conditions.

In some embodiments, the *Clostridium saccharoperbutylacetonicum* may be sporulation-deficient due to the presence of a mutation in at least one gene which is associated with sporogenesis, wherein the mutation reduces the ability of the *Clostridium saccharoperbutylacetonicum* to sporulate or delays the ability of the *Clostridium saccharoperbutylacetonicum* to sporulate compared to a *Clostridium saccharoperbutylacetonicum* of the same species which possesses the wild-type form of the gene.

In some embodiments, the gene associated with sporogenesis is a spo gene. Examples of spo genes include spo0, spoII, spoIII, spoIV, spoV, spoVI and spoIX genes.

Preferably, the gene associated with sporogenesis is a spo0 gene, more preferably spo0A or spo0E, and most preferably spo0A.

In other embodiments, the gene associated with sporogenesis encodes a sigma factor, a sigma factor processing protein, or a protein required for the transcription and/or translation and/or obtaining a fully functional form of a sigma factor.

Examples of genes associated with sporogenesis which encode a sigma factor include the following:

sigE (annotated as CAC1695 on *C. acetobutylicum* ATCC 824; GenBank #NC-003030.1, GeneID 1117878), sigG (annotated as CAC1696 on *C. acetobutylicum* ATCC 824; GenBank #NC-003030.1, GeneID 1117879), sigF (annotated as CAC2306 on *C. acetobutylicum* ATCC 824, GenBank #NC-003030.1, GeneID 1118489), sigH, CAP0157 (GenBank AAK76902), CAP0167 (GenBank AAK76912), CAC3267 (GenBank #NC-003030.1, GeneID 1119449), CAC1766 (GenBank #NC-003030.1, GeneID 1117949), CAC2052 (GenBank #NC-003030.1, GeneID 1118235), CAC0550 (GenBank #NC-003030.1, GeneID 1116733), CAC2053 (GenBank #NC-003030.1, GeneID 1118236), CAP0166 (GenBank AAK76911),

*C. beijerinckii* NCIMB 8052 (GenBank #CP000721, Refseq NC-009617);

*C. thermocellum* ATCC27405 (GenBank #CP000568, Refseq NC-009012);

*C. cellulolyticum* H10 (GenBank #AAVC00000000, Refseq NZ_AAVC00000000, unfinished);

*C. butyricum* 5521 (GenBank #ABDT00000000, Refseq NZ ABDT00000000, unfinished);

*C. phytofermentans* ISDg (GenBank #CP000885, Refseq NC-010001).

The mutation of the gene associated with sporogenesis may result in the gene encoding a mutated polypeptide which has a deletion, insertion or substitution of one or more amino acids. In other embodiments, the mutation of the gene associated with sporogenesis results in the gene being knocked-out, eliminated or down-regulated. The term "mutated" includes mutations in a regulatory region of the gene, e.g. promoter or terminator which affects the expression of the gene.

In embodiments of the invention wherein the gene associated with sporogenesis encodes a mutated Spo0A polypeptide, the mutation is preferably in the C-terminal end of the Spo0A polypeptide. Preferably, the mutation is within amino acids 250-273 of the Spo0A polypeptide.

More preferably, the mutation is at a position which corresponds to or encompasses amino acid 261 of SEQ ID NO: 1.

In some embodiments, the gene associated with sporogenesis encodes a mutated Spo0A polypeptide which has an amino acid substitution at the position which corresponds to amino acid 261 of SEQ ID NO: 1. Preferably, the substitution is T for I (as shown in SEQ ID NO: 2).

Corresponding sequences and percentage amino acid and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and http://www.ncbi.nlm.nih.gov/BLAST). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules (e.g. Altschul et al. (1997) supra). When utilizing BLAST, Gapped BLAST, PSI-BLAST, the default parameters of the respective programs may be used.

With regard to nucleotide sequence comparisons, MEGA-BLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

In some embodiments, the term "sporulation-deficient" refers to *Clostridium* strain which has a relative colony forming efficiency (survival rate) of a culture of less than about $1 \times 10^{-2}$, less than about $1 \times 10^{-3}$, less than about $1 \times 10^{-4}$, less than about $1 \times 10^{-6}$, less than about $1 \times 10^{-6}$, less than about $1 \times 10^{-7}$, less than about $1 \times 10^{-8}$ or less than about $1 \times 10^{-9}$.

Sporulation-deficiencies may be measured by any of the methods described herein. For example, a culture of actively growing *Clostridium saccharoperbutylacetonicum* (growing in a medium where gamma cyclodextrin is the main or only carbohydrate source) may be subjected to a heat shock, which will kill vegetative cells but not kill spores, of 70 or 80 or 90 or 100° C. for ten or five minutes (preferably 80° C. for 10 minutes) and the relative colony forming efficiency measured against an untreated culture or aliquot of the culture that has not been subjected to the same heat shock.

Alternatively, a culture of actively growing *Clostridium saccharoperbutylacetonicum* (growing in a medium where gamma cyclodextrin is the main or only carbohydrate source) may be subjected to chloroform treatment, which will kill vegetative cells but not kill spores, e.g. combining 0.5 ml of culture with 0.5 ml of >99% chloroform, incubating with mild agitation for 10 minutes, and then plating serial dilutions of the aqueous phase, e.g. using CGM-agar plates.

In yet a further embodiment, the invention provides a *C. saccharoperbutylacetonicum* mutant strain, wherein the genome of the mutant strain encodes a mutated Spo0A polypeptide which has an amino acid substitution at the position which corresponds to amino acid 261 of SEQ ID NO: 1 (i.e. the encoded Spo0A polypeptide does not have isoleucine at the position which corresponds to amino acid 261 of SEQ ID NO: 1).

Preferably, the amino acid substitution is T for I (as shown in SEQ ID NO: 2). Preferably, the mutant is a mutant of *C. saccharoperbutylacetonicum* N1-4(HMT) or N1-504.

The process of the invention is preferably a single stage process. As used herein, the term "single stage" means that bio-products are co-produced, for example both acid(s) and solvent(s) are produced together in the same culture vessel using a monophasic *Clostridium saccharoperbutylacetonicum*. This may be contrasted with a two-stage process wherein some bio-products (e.g. organic acids) are produced in a first growth stage and other bio-products (e.g. solvents) are subsequently produced in a second stage, and these two stages are performed in two separate culture vessels.

The *Clostridium saccharoperbutylacetonicum* strain may be an aerobic or an anaerobic microorganism. Preferably, it is an anaerobic or aero-tolerant *Clostridium saccharoperbutylacetonicum* strain. Most preferably, it is an aero-tolerant *Clostridium saccharoperbutylacetonicum* strain.

In some embodiments, the culture vessel may be inoculated with no special precautions taken to exclude oxygen or no anaerobic purge. Furthermore, the culture vessel may be operated with air (of normal atmosphere composition) in the head-space above the culture medium.

In some embodiments of the invention, the process is performed under conditions which are not oxygen-free.

In some embodiments, the *Clostridium saccharoperbutylacetonicum* cells are acid-tolerant. The *Clostridium saccharoperbutylacetonicum* cells can preferably tolerate high concentrations of R—COOH. In this context, high concentrations of R—COOH may mean up to 15 g/L acetic acid, and/or up to 10 g/L lactic acid and/or up to 6 g/L formic acid.

In some embodiments, some or all of the *Clostridium saccharoperbutylacetonicum* cells may be immobilised in the culture vessel. In other embodiments, the *Clostridium saccharoperbutylacetonicum* cells are non-immobilised or are in free suspension. The cells could be immobilized by active immobilization techniques, whereby free suspended cells are immobilized by covalent attachment to surfaces, cross-linking of cells to surfaces, entrapment within gels or membrane confinement; or by passive immobilization, exploiting the natural tendency of cells to adhere to solid porous surfaces due to electrostatic interactions or by their ability to form films or aggregates around or within a support material.

The preferred methods for immobilizing *Clostridium saccharoperbutylacetonicum* cells are:

(i) entrapment of cells within a gel matrix made of naturally occurring polymers (e.g. alginates, kappa-carrageenan, collagen, gelatine, cellulose, etc.) or synthetic gels (polyacrylamide, polymethacrylamide, photo-cross-linkable resin pre-polymers, urethane pre-polymers, polyethyleneglycol and polyvinyl alcohol, etc.); and (ii) membrane confinement of cells by immobilization behind a barrier. The barriers can be droplets of cell-water suspensions emulsified in organic solvents or semi-permeable membranes.

The culture vessel may be any form of culture vessel which is suitable for culturing the *Clostridium saccharoperbutylacetonicum* cells in the process of the invention. Preferred types of culture vessel include conventional stirred bioreactors.

As used herein, the term "culture vessel" includes two or more culture vessels which may or may not be linked in fluid communication. Any multiple culture vessels may be linked in parallel or in series.

In the context of the invention, however, the acid(s) and solvent(s) are preferably both produced together (i.e. in a mixture) in a single culture vessel. It is not the case that one or more acids are produced in a first culture vessel and they are then converted to one or more solvents in a second culture vessel.

In one embodiment, one or more bio-products are produced together in a single vessel. In another embodiment, different bio-products are generated in the first and second vessels, which may be supplied with different substrates.

The *Clostridium saccharoperbutylacetonicum* cells in the culture vessel are maintained under conditions which are suitable for them to produce the desired bio-products (e.g. organic acids and/or solvents).

Suitable liquid culture media are well known in the art. These will be selected according to the *Clostridium saccharoperbutylacetonicum* strain which is being used. Generally, the culture medium will be an aqueous culture medium.

The culture medium comprises gamma-cyclodextrin as a carbon source, optionally together with one or more other carbon sources.

As used herein, the term "carbon source" refers to sources of utilisable or assimilable carbon-containing compounds which can be used by the *Clostridium* to make the basic components of the bacterial cell (cell mass). Carbon is required, for example, for the production of molecules such as lipids, nucleic acids, amino acids and sugars. In most bacteria, including *Clostridium*, the carbon source is also used to generate energy for life and growth. In some embodiments, the carbon source is also used to produce the desired bio-products.

Examples of other carbon sources include organic carbon sources such as carbohydrates (saccharides), e.g. monosaccharides, disaccharides, oligosaccharides and polysaccharides, sugar alcohols and amino acids; and inorganic carbon sources such as carbon monoxide and carbon dioxide. The choice of suitable carbon source will be led by the presence of the relevant metabolic pathways present (naturally or engineered) in the chosen *Clostridium saccharoperbutylacetonicum*.

Preferred mono- and di-saccharides include C5 and C6 sugar monomers, and C5 and C6 sugar dimers.

Preferred sugars are arabinose, xylose, mannose, fructose, glucose, galactose, sucrose, lactose, maltose and cellobiose. Preferably, the sugars are hydrolysates derived from lignocellulosic feedstocks such as agricultural residues (e.g. from corn & sugar production), woody residues, energy crops or municipal waste. In another embodiment, the sugars are hydrolysates derived from a starch-based material. In yet another embodiment, the sugars are sucrose from feedstocks such as molasses, sugar beet or sugar cane.

Preferred polysaccharides are starch, xylan, pectin, fructan, cellulose and mannan, most preferably starch and cellulose.

The polysaccharide/carbohydrate may also be a glucose-based polysaccharide, e.g. a starch or a starch-based material. Most preferably, the carbohydrate/polysaccharide is starch or a starch-based material, e.g. corn, corn starch, corn mash, potato, potato starch, potato mash, potato peeling, potato chips, cassava, cassava starch, cassava chips, sago, sago starch, dextrin or 'soluble starch', e.g. as sold by Fisher/Sigma. Further examples of polysaccharides derived from starch hydrolysis include cyclodextrins, such as alpha- and beta-cyclodextrins and the cyclodextrin that is naturally produced by the *C. saccharoperbutylacetonicum* N1-4 (HMT) CGTase enzyme.

Suitable sugar alcohols include glycerol (also known as glycerine), mannitol and sorbitol. In some embodiments, the other carbon source does not comprise glucose.

A key aspect of this invention is that the *Clostridium saccharoperbutylacetonicum* is cultured in a liquid culture medium in a culture vessel, wherein the culture medium comprises gamma-cyclodextrin.

As used herein, the term "gamma-cyclodextrin" refers to a cyclic oligosaccharide which is composed of eight α-(1,4) linked glucopyranose subunits.

Figure 11:
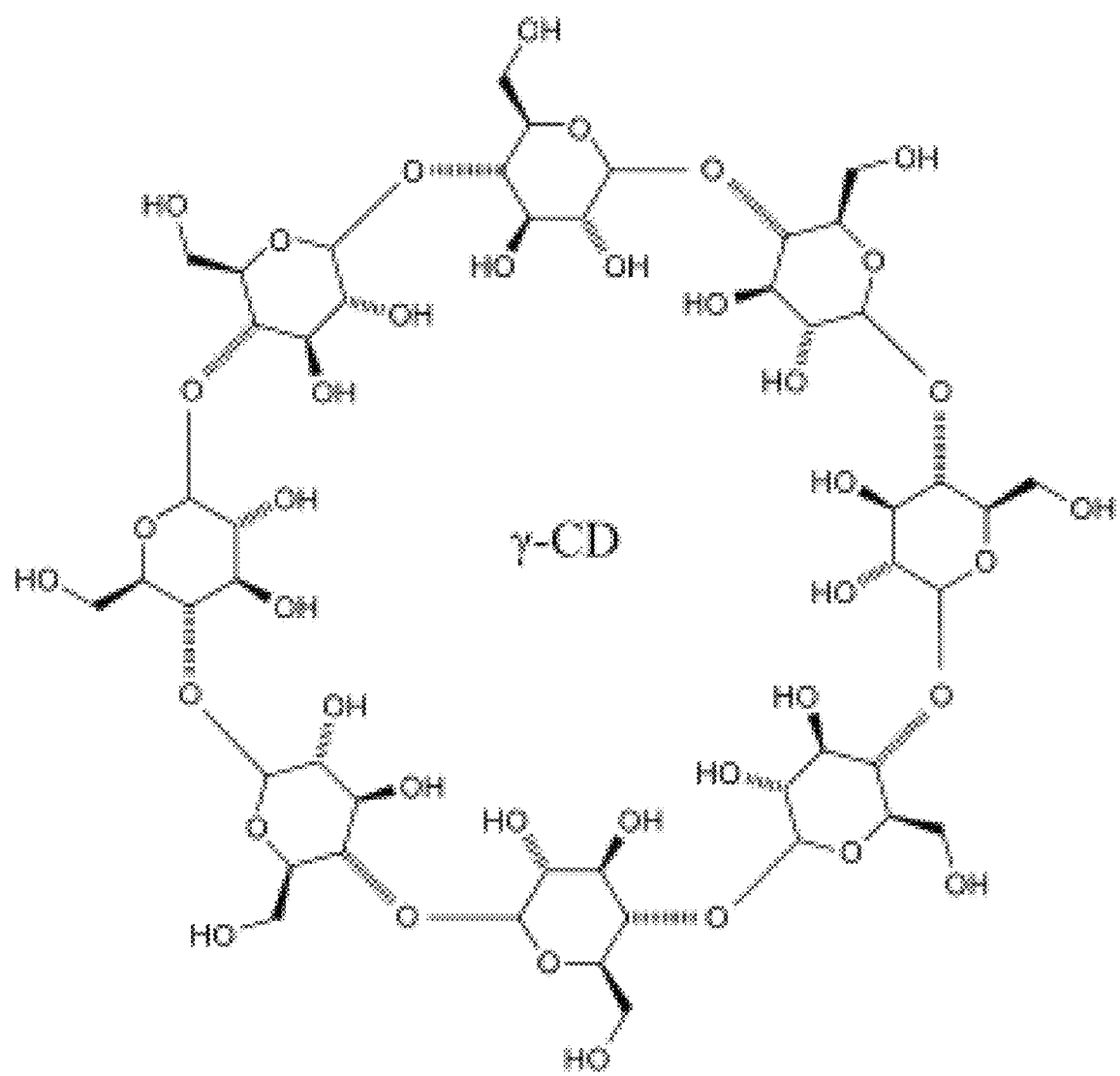
FIG. 11: One example of a gamma-cyclodextrin.

One example of a gamma-cyclodextrin is shown in FIG. 11.

In some embodiments, the cyclodextrin is substituted at the 2, 3, and/or 6 hydroxyl sites in order to increase solubility, preferably with methyl groups.

Cyclodextrins may be produced by the treatment of starch with cyclodextrin glycosyltransferase (CGTase) enzymes. Alpha-amylase is often additionally used. Starch is first liquified either by heat-treatment or using alpha-amylase; CGTase then is added for the enzymatic conversion. CGTases can synthesize multiple forms of cyclodextrins: thus the product of the conversion often results in a mixture of the three main types of cyclic molecules, in ratios that are strictly dependent on the enzyme used. Each CGTase has its own characteristic alpha:beta:gamma synthesis ratio.

Purification of the three types of cyclodextrins takes advantage of the different water solubility of the molecules. Beta-CD which is very poorly water-soluble (18.5 g/L or 16.3 mM at 25° C.) can be easily retrieved through crystallization, while the more soluble alpha- and gamma-CDs (145 and 232 g/L, respectively) are usually purified by means of expensive and time-consuming chromatography techniques. As an alternative, a "complexing agent" can be added during the enzymatic conversion step. Such agents (usually organic solvents such as toluene, acetone or ethanol) form a complex with the desired cyclodextrin which subsequently precipitates. The complex formation drives the conversion of starch towards the synthesis of the precipitated cyclodextrin, thus enriching its content in the final mixture of products. Wacker Chemie AG uses dedicated enzymes that can produce alpha-, beta- or gamma-cyclodextrin specifically.

Preferably, the gamma-cyclodextrin is obtained from an industrial feedstock such as a starch or a starch-based material (e.g. as defined herein).

The culture medium comprises or is being fed (e.g. via a feedstock, pumped into the culture vessel) gamma-cyclodextrin as a carbon source. Other carbon sources may also be present in the culture medium or in the culture medium feed.

In some embodiments, a liquid feedstock is introduced into the culture vessel. In such embodiments, a reservoir of liquid feedstock is in liquid communication with the culture vessel. The feedstock may be introduced into the culture vessel continuously or discontinuously (depending on conditions with the culture vessel).

In some embodiments, the feedstock is starch (e.g. from corn) that has been contacted with appropriate catalysts (e.g. enzymes or microorganisms) to generate gamma-cyclodextrin.

In some embodiments, the feedstock contains, in addition to gamma-cyclodextrin, other carbon sources that are possible by-products of the conversion of starch to gamma-cyclodextrin, such as other cyclodextrins. It may also contain other carbon sources that are commonly found in starchy feedstocks, and degradation products thereof, such as starch, linear dextrins, branched dextrins maltose and glucose.

The *Clostridium saccharoperbutylacetonicum* cells are cultured under conditions which promote the growth of the *Clostridium saccharoperbutylacetonicum* cells and/or the production of one or more of the desired bio-products, e.g. solvents, such as butanol.

As mentioned above, there is a constant risk in industrial fermentation processes of contamination of the desired *Clostridium saccharoperbutylacetonicum* cells with other (undesired or contaminating) micro-organisms.

In some embodiments, in the process of the invention, the *Clostridium saccharoperbutylacetonicum* cells are cultured under conditions which favour the growth of the *Clostridium saccharoperbutylacetonicum* cells. In particular, these conditions favour the growth of the *Clostridium saccharoperbutylacetonicum* cells over a contaminating bacterium (e.g. a lactic acid bacterium, e.g. *Lactobacillus delbrueckii*).

More preferably, in the process of the invention, the concentration or amount of all utilisable carbon sources (including the gamma-cyclodextrin) in the culture medium in the culture vessel and/or in the culture medium feedstock is one which favours the growth of the *Clostridium saccharoperbutylacetonicum* cells in the culture vessel.

In particular, this concentration or amount favours the growth of the *Clostridium saccharoperbutylacetonicum* cells over a contaminating bacterium (e.g. a lactic acid bacterium, e.g. *Lactobacillus delbrueckii*).

As used herein, the term "contaminating bacterium" is a bacterium whose presence is not desired in the culture vessel.

The "contaminating bacterium" is preferably one which is not capable of utilising gamma-cyclodextrin as a carbon source.

Generally, the contaminating bacterium is one that is not part of the defined bacterial culture, for example the contaminating bacterium is not a bacterium that is involved in producing the desired bio-product.

The contaminating bacterium is one that is not deliberately added to the reaction vessel(s) as part of the process.

In some embodiments, the contaminating bacterium is a lactic acid bacterium. The term lactic acid bacterium is defined by Todar's online textbook of microbiology (http://textbookofbacteriology.net/lactics.html) as being "conventionally reserved for genera of the order Lactobacillales, which includes *Lactobacillus, Leuconostoc, Pediococcus, Lactococcus* and *Streptococcus*, in addition to *Carnobacterium, Enterococcus, Oenococcus, Tetragenococcus, Vagococcus,* and *Weisella.*"

In some embodiments, the contaminating bacterium is from the family Lactobacillaceae. In some embodiments, the contaminating bacterium is from the order Lactobacillales. In some embodiments, the contaminating bacterium is a *Lactobacillus*. In some embodiments, the contaminating bacterium is *Lactobacillus delbrueckii* or *Lactobacillus casei*. In other embodiments, the contaminating bacterium is a *Pediococcus*. In other embodiments, the contaminating bacterium is *Pediococcus acidilactici*. In other embodiments, the contaminating bacterium is from the class Bacilli. In other embodiments, the contaminating bacterium is a solventogenic bacterium. In other embodiments, the contaminating bacterium is a solventogenic bacterium that has not been added to the vessels or process deliberately. In other embodiments, the contaminating bacterium is a solventogenic *Clostridium* sp. that has not been added to the vessels or process deliberately. In other embodiments, the contaminating bacterium is a non-solventogenic bacterium. In other embodiments, the contaminating bacterium is not a *Clostridium*. In other embodiments, the contaminating bacterium is a *Clostridium* sp. which is not a *C. saccharoperbutylacetonicum* strain. In other embodiments, the contaminating bacterium is not a solventogenic *Clostridium*. In other embodiments, the contaminating bacterium is a *Clostridium* sp. which does not grow or not grow well on gamma-cyclodextrin (e.g. *C. acetobutylicum, C. tyrobutyricum, C. beijerinckii*).

The relative growth of the *Clostridium saccharoperbutylacetonicum* cells compared to that of the contaminating bacteria may be measured by microscopy (e.g. at 40× magnification as described in the Examples herein). Appropriate staining methods may be used for distinguishing bacteria of different types.

A genomics approach could also be used: Samples (e.g. 100 µl) of culture can be transferred to DNA collection cards (e.g. GE Healthcare, Whatman FTA™ Nucleic Acid Collection Cards). The presence of contaminating bacteria in these samples, e.g. various lactic acid bacteria, can be determined by PCR, using primers designed for specific types of bacteria. (Primer design can be based on knowledge of likely contaminants, for example using metagenomic data from previous fermentations.)

In some embodiments of the invention, gamma-cyclodextrin is the primary utilisable carbon source for the *Clostridium saccharoperbutylacetonicum* cells of the defined culture in the culture medium or the carbon source which is primarily utilised by the *Clostridium saccharoperbutylacetonicum* of the defined culture cells in the culture medium.

The skilled person will be aware of the fact that during the culture of the *Clostridium saccharoperbutylacetonicum* cells, the ratio of carbon sources which are present in the culture vessel may be very different to what is initially provided in the culture vessel or what is fed into the culture vessel (as the culture feedstock) during the process. This is due to the different carbon-source preferences of the *Clostridium saccharoperbutylacetonicum* cells. For example, when provided with a mixture of glucose and xylose, *C. saccharoperbutylacetonicum* N1-4 (HMT) will tend to use up most of the glucose, thus allowing the xylose to accumulate. It is expected that, if *C. saccharoperbutylacetonicum* N1-4 (HMT) was provided with a mixture of gamma-cyclodextrin and another less preferable sugar or sugar precursor, e.g. alpha-cyclodextrin, then the aforementioned bacterium would preferentially use gamma-cyclodextrin, which could mean that the gamma-cyclodextrin concentration in the culture vessel would be close to zero, while the other, less preferable, sugar or sugar precursor concentration would be higher. Hence the absolute concentration of the carbon source in the culture vessel is not an appropriate indicator of the carbon-source preferences of the bacterium.

As used herein, the term "primary" or "primarily" refers to the fact that the carbon source with the highest concentration (g/L) in the supplied culture medium (e.g. in the culture feedstock) is gamma-cyclodextrin.

As used herein, the term "utilisable" means that the carbon source is assimilable into the *Clostridium saccharoperbutylacetonicum* cells, i.e. the carbon source is capable of being broken down to carbon-based molecules which can be assimilated into metabolic pathways in the *Clostridium* cells.

In yet another embodiment, the carbon source in the culture medium consists essentially of gamma-cyclodextrin. In yet another embodiment, gamma-cyclodextrin is the only carbon source in the culture medium.

In some embodiments of the invention, the culture medium at the start of the process or during the process comprises 0.5-20% or 1-10%, preferably 2-9% or 3-7%, more preferably 4-6%, and most preferably about 5% (i.e. 50 g/L), total cyclodextrin.

In some embodiments of the invention, the culture medium at the start of the process or during the process comprises 0.5-20% or 1-10%, preferably 2-9%, 3-7%, more preferably 4-6%, and most preferably about 5% (i.e. 50 g/L), gamma-cyclodextrin.

In practice, the concentration of the feedstock into the culture vessel may be adapted to provide the desired concentration of cyclodextrin/gamma-cyclodextrin in the culture vessel.

In some embodiments of the invention, the culture medium at the start of the process or during the process comprises less than 10%, more preferably less than 8%, 6%, 4% or 2%, and most preferably less than 1% (i.e. 10 g/L) utilisable or assimilable carbon-sources other than cyclodextrins.

Preferably, the culture medium at the start of the process or during the process comprises less than 10%, more preferably less than 8%, 6%, 4% or 2%, and most preferably less than 1% (i.e. 10 g/L) utilisable or assimilable carbon-sources other than gamma-cyclodextrin.

In some embodiments of the invention, the culture medium at the start of the process or during the process does not comprise starch or cellulose.

In other embodiments, the culture medium at the start of the process or during the process does not comprise any (added) mono- or di-saccharides.

In other embodiments, the culture medium at the start of the process or during the process does not comprise any oligo- or polysaccharides other than cyclodextrins.

Preferably, the culture medium at the start of the process or during the process does not comprise any oligo- or polysaccharides other than gamma-cyclodextrin.

The pH of the culture vessel may be controlled through the automated addition of alkali from a separate alkali feed or from the addition of feed media that has a pH lower than the culture vessel's (typically 1-2 pH units). The pH of the culture vessel is preferably pH 5.0-7.0, more preferably pH 5.5-6.5.

The pH may also be controlled by a pH auxostat. Preferably, the pH-auxostat has a separate alkali feed and the pump is linked to the pump controlling the media feed. The cell density in the culture vessel may be controlled by altering the ratio or relative speed of the alkali-feed and media-feed pumps.

The temperature will be selected as being one at which the microorganism grows best. For example, for mesophilic *Clostridium saccharoperbutylacetonicum* the temperature is preferably 30-37° C., more preferably 31-33° C., e.g. about 32° C.

The *Clostridium saccharoperbutylacetonicum* convert substrates based on carbohydrates, e.g. sugars, sugar precursors and/or starches, into bio-products. These bio-products could include organic acids (e.g. RCOOH, wherein R is as defined herein). Exemplary acids include acetic acid and/or butyric acid. The acid concentration may be monitored by gas chromatography (GC) or high performance liquid chromatography (HPLC).

The production of these acids may also be monitored by a change in culture pH. In this case, the monitoring apparatus may be a pH meter.

Cell density may be monitored by optical means, for example by determining the optical density (OD) at 600 nm.

In other embodiments, a change in cell density may be linked to a change in the rate of fresh media/nutrient feed or removal of culture media comprising solvent(s), e.g. by using a turbidostat.

The production of one or more bio-products, which could include solvents (e.g. ethanol, butanol, acetone) may be monitored by gas chromatography (GC) and/or high performance liquid chromatography (HPLC), and/or other analytical techniques known in the art to be suitable for measurement of the specific bio-products.

Preferably, the butanol concentration in the culture vessel should not exceed 10 g butanol $L^{-1}$.

The utilisation of one or more sugars (e.g. glucose, xylose, fructose, arabinose, sucrose, cellobiose, or others as appropriate depending on the feedstock) and gamma-cyclodextrin may be monitored by HPLC, and/or other analytical techniques known in the art to be suitable for measurement of such sugars.

Preferably, the sugar concentration in the culture vessel (excluding gamma-cyclodextrin) should not exceed 30 g sugar $L^{-1}$.

The method of separating or removing the bio-product from the cells or the culture medium will depend upon the properties of the bio-product.

The liquid culture medium from the culture vessel may be passed directly or indirectly to a cell separator.

The residual liquid culture medium may be passed directly or indirectly back to the culture vessel, e.g. it may be stored temporarily, e.g. in a reservoir.

In order to reduce loss of cells from the culture vessel, a cell separator may be positioned upstream of a bio-product removal system, e.g. a solvent remover. In the cell separator, all or a substantial portion of the cells are removed from the stream or portion of the liquid culture medium which is passed through the cell separator. For example, the cell separator may remove at least 50%, preferably at least 70%, and most preferably at least 80% or at least 90% of the cells from the liquid culture medium which is passed through the cell separator. Examples of cell separators include hollow fibre separators, membrane separators and centrifugal separators.

In embodiments of the invention wherein the bio-product is a solvent, the remaining liquid may then be passed to a solvent remover.

The liquid culture medium which is removed from the culture vessel will be enriched in one or more solvents which have been produced by the solventogenic *Clostridium saccharoperbutylacetonicum*.

Preferably, liquid culture medium starts to be removed from the culture vessel once the solvent(s) produced in the culture vessel reach a defined concentration point (e.g. 8-10 g butanol $L^{-1}$ liquid culture media).

The liquid culture medium should preferably be passed to a solvent remover at a rate which maintains the solvent concentration in the liquid culture medium below the desired solvent concentration point. This concentration point may, for example, be the toxicity threshold for the specific solventogenic *Clostridium saccharoperbutylacetonicum* used.

Generally, the solvent(s) will be recovered from the liquid culture medium (fermentation broth) by one or more of liquid-liquid extraction, ionic-liquid extraction, gas stripping, vacuum evaporation, atmospheric or vacuum distillation, pervaporation, ion-exchange adsorption, counter-current solvent extraction and/or distillation. Alternatively, hydrophobic membranes may be used, e.g. with air flux or inert gas carrier or vacuum (pervaporation) to aid the separation (preferably in a continuous process).

Preferably, the solvent(s) will be recovered from the liquid culture medium by atmospheric or vacuum distillation, pervaporation, liquid-liquid extraction and/or gas stripping. Preferably, the solvent extraction is performed continuously.

In some embodiments of the invention, solvent may be produced at a rate of at least 0.8 $g \cdot L^{-1} \cdot h^{-1}$ for periods in excess of 60 hours or 0.6 $g \cdot L^{-1} \cdot h^{-1}$ for over 100 hours.

In some more preferable embodiments, solvent extraction is via continuous atmospheric or vacuum distillation.

Once the solvents are removed from the liquid culture medium, some or all of the residual liquid culture medium is returned to the culture vessel. This maximizes utilization of nutrients from the liquid culture medium and minimises water loss.

In the simplest version of the fermentation process a single batch seed of 5-10% v/v can be used to inoculate the fermentation at the beginning of the fermentation. However, it is possible also to use multiple batch inoculations of 5-10% v/v at various time intervals during the fermentation in order to maintain high cell densities and solvent productivities. Alternatively, continuous culture can be used to provide a continuous supply of fresh cells to the culture vessel. The preferred embodiment is a pH-auxostat that is fed from the still bottoms from distillation and self-regulated using a set pH value to control the addition of feed and/or fresh nutrients and sugars.

The invention also provides a bio-product, e.g. a solvent, preferably butanol, which has been produced by a process of the invention.

In yet another embodiment, the invention provides a process for reducing or eliminating growth of a contaminating bacterium in a culture medium comprising *Clostridium saccharoperbutylacetonicum* cells, the process comprising the steps:
(a) culturing *Clostridium saccharoperbutylacetonicum* cells in a liquid culture medium in a culture vessel, wherein the culture medium comprises one or more carbon sources but does not comprise gamma-cyclodextrin, wherein the *Clostridium saccharoperbutylacetonicum* cells are ones which are capable of utilising gamma-cyclodextrin as a carbon source, wherein the culture medium comprises sufficient carbon sources to support growth of the *Clostridium saccharoperbutylacetonicum* cells, wherein the culture vessel additionally comprises a contaminating bacterium which is not capable of utilising gamma-cyclodextrin as a carbon source; and
(b) increasing the concentration of gamma-cyclodextrin in the culture medium and reducing the concentration of at least one of the said other carbon sources in the culture medium to concentrations wherein the growth of the *Clostridium saccharoperbutylacetonicum* cells is favoured over the growth of the contaminating bacterium;

thereby reducing or eliminating growth of the contaminating bacterium in the culture vessel.

In some embodiments, Step (b) comprises:
(b) increasing the concentration of gamma-cyclodextrin in the culture medium and removing said other carbon sources from the culture medium such that the growth of the *Clostridium saccharoperbutylacetonicum* cells is favoured over the growth of the contaminating bacterium.

In yet another embodiment, the invention provides a process for reducing or eliminating growth of a contaminating bacterium in a culture medium comprising *Clostridium* cells, the process comprising the steps:

(a) culturing *Clostridium saccharoperbutylacetonicum* cells in a liquid culture medium in a culture vessel, wherein the *Clostridium saccharoperbutylacetonicum* cells are ones which are capable of utilising gamma-cyclodextrin as a carbon source, wherein the culture medium comprises gamma-cyclodextrin as a carbon source and additionally one or more other carbon sources, wherein the culture medium comprises sufficient carbon sources to support growth of the *Clostridium saccharoperbutylacetonicum* cells, wherein the culture vessel additionally comprises a contaminating bacterium which is not capable of utilising gamma-cyclodextrin as a carbon source; and (b) reducing the concentration of at least one of the said other carbon sources in the culture medium to a concentration wherein the growth of the *Clostridium saccharoperbutylacetonicum* cells is favoured over the growth of the contaminating bacterium;

thereby reducing or eliminating growth of the contaminating bacterium in the culture vessel.

In some embodiments, Step (b) comprises:

(b) increasing the concentration of gamma-cyclodextrin in the culture medium and reducing the concentration of at least one other carbon source in the culture medium to concentrations wherein the growth of the *Clostridium saccharoperbutylacetonicum* cells is favoured over the growth of the contaminating bacterium.

In other embodiments, Step (b) comprises:

(b) increasing the concentration of gamma-cyclodextrin in the culture medium and removing said other carbon sources from the culture medium such that the growth of the *Clostridium saccharoperbutylacetonicum* cells is favoured over the growth of the contaminating bacterium.

The said other carbon sources may be removed from the culture medium by, for example, dilution with new medium or by replacement of the culture medium, or by consumption by microorganisms.

The invention also provides a system for the production of a bio-product, the system comprising:

(i) a culture vessel comprising *Clostridium saccharoperbutylacetonicum* cells in a liquid culture medium; and optionally (ii) monitoring apparatus for monitoring growth of cells in the culture vessel;

wherein the *Clostridium saccharoperbutylacetonicum* cells are ones which are capable of producing the bio-product, wherein the *Clostridium saccharoperbutylacetonicum* cells are ones which are capable of utilising gamma-cyclodextrin as a carbon source, and wherein the liquid culture medium comprises gamma-cyclodextrin as a carbon source, and optionally one or more other carbon sources.

The system is preferably adapted to carry out a process of the invention. Also provided is a use of a system of the invention in a process of the invention.

The disclosure of each reference set forth herein is incorporated herein by reference in its entirety.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Competition of *Clostridium* and *Lactobacillus* in Fermentations Based on Glucose or Gamma-Cyclodextrin A 2×TYIR nutrient stock (5 g/L yeast extract, 5 g/L tryptone, 50 mg/L $FeSO_4.7H_2O$, 1 g/L $(NH_4)_2SO_4$ and 10 g/L $CaCO_3$) and individual 10% sugar stocks (100 g/L) of glucose or gamma-cyclodextrin were prepared and sterilised separately by autoclaving for 15 min at 121° C. Equal volumes of 2× nutrient stock and either 10% glucose or 10% gamma-cyclodextrin were pipetted into sterile serum bottles to give a working volume of 60 mL, with final concentrations of 1×TYIR and 5% sugar. The bottles were incubated at 32° C. in an anaerobic cabinet for 24 h prior to inoculation with starter culture.

Starter cultures were prepared by 1) inoculating 30 mL of pre-warmed, anaerobic RCM medium with an RCM-reconstituted *Clostridium saccharoperbutylacetonicum* freeze-dried stock, and by 2) inoculating 10 mL of pre-warmed, anaerobic MRS medium with a *Lactobacillus delbrueckii* 30% glycerol stock. Both cultures were incubated anaerobically at 32° C. for approximately 18 h, until an OD of 1.5-1.6 was reached.

("RCM" (Reinforced Clostridial Medium) was prepared from OXOID™ product CM0149 according to the manufacturer's instructions, to give final concentrations: 13 g/L yeast extract, 10.0 g/L peptone, 5 g/L glucose, 1 g/L soluble starch, 5 g/L sodium chloride, 3 g/L sodium acetate, 0.5 g/L cysteine hydrochloride, 0.5 g/L agar, pH 6.8±0.2.)

("RCM-agar is prepared as above but with the addition of 15 g/l bacteriological-grade agar.) ("MRS" (de Man, Rogosa & Sharpe broth) was prepared from OXOID™ product CM0359 according to the manufacturer's instructions, to give final concentrations:

10 g/L peptone, 8 g/L 'Lab-Lemco' powder, 4 g/L yeast extract, 20 g/L glucose, 1 mL/L sorbitan mono-oleate, 2 g/L dipotassium hydrogen phosphate, 5 g/L sodium acetate $3H_2O$, 2 g/L triammonium citrate, 0.2 g/L magnesium sulphate $7H_2O$, 0.05 g/L manganese sulphate $4H_2O$, pH 6.2±0.2 at 25° C.)

Triplicate control screen bottles of TYIR-glucose or TYIR-gamma-cyclodextrin were inoculated with 3 mL of *C. saccharoperbutylacetonicum* starter culture (5% inoculum), or with 3 mL of *L. delbrueckii* starter culture (5% inoculum), or with 3 mL of each starter culture (6 mL total inoculum volume). Cultures were incubated anaerobically at 32° C. for 72 h and sampled at 24 h, 48 h and 72 h by removing 1 mL from each bottle. Differences in *Clostridium* and *Lactobacillus* cell numbers under each condition were determined by microscopy at 40× magnification. Cell-free culture supernatants were analysed by HPLC to quantify residual sugar (g/L) in the growth medium and production of acetone, ethanol, butanol and lactic acid (g/L), and the results of these are shown in FIG. 1.

Both the *C. saccharoperbutylacetonicum* and *L. delbrueckii* pure cultures were able to use glucose as a carbon source to produce 12 g/L butanol or 9 g/L lactic acid, respectively. No butanol was detected in the mixed culture but lactic acid was present throughout the screen, with a total titre of 15 g/L reached by 72 h; significantly higher than the pure culture control. These data correlate with the microscopy, where fewer *Clostridium* cells were observed in the mixed culture compared with *Lactobacillus* cells. Together, these results show that *L. delbrueckii* outcompeted *C. saccharoperbutylacetonicum* when grown on glucose.

The *C. saccharoperbutylacetonicum* cells were able to metabolise gamma-cyclodextrin; healthy, motile cultures were observed across the triplicate samples and butanol titres reached a total of 13-14 g/L. In contrast, no *L. delbrueckii* growth was observed by microscopy and no lactic acid production was detected in the pure culture control. The mixed culture data correlated with the pure culture controls; 13-14 g/L of butanol was produced with no trace of lactic acid.

In summary, these data show that use of gamma-cyclodextrin as the sole carbon source prevented *L. delbrueckii* from outcompeting *C. saccharoperbutylacetonicum* during fermentation.

Example 2: Testing Growth of Bacteria on Alpha-Cyclodextrin and on Beta-Cyclodextrin A 2×TYIR nutrient stock and individual 10% carbohydrate stocks (100 g/L) of glucose or alpha-cyclodextrin were prepared and sterilised separately for 15 min at 121° C. Equal volumes of 2× nutrient stock and either 10% glucose or 10% alpha-cyclodextrin were pipetted into 15 mL tubes to give a working volume of 10 mL, with final concentrations of 1×TYIR and 5% carbohydrate. The tubes were incubated at 32° C. in an anaerobic cabinet for 24 h prior to inoculation with starter culture. Starter cultures were prepared for three different bacteria (1) *C. saccharoperbutylacetonicum* N1-4 (HMT), (2) *C. saccharoperbutylacetonicum* N1-504 and (3) *Lactobacillus delbrueckii* as follows:

For (1) and (2) 30 mL lots of pre-warmed, anaerobic RCM medium were inoculated with an RCM-reconstituted *C. saccharoperbutylacetonicum* N1-504 freeze-dried stock, or an RCM-reconstituted *C. saccharoperbutylacetonicum* N1-4 (HMT) freeze-dried stock, respectively) and for (3) a 10 mL lot of pre-warmed, anaerobic MRS medium was inoculated with a *L. delbrueckii* 30% glycerol stock. All three starter cultures were incubated anaerobically at 32° C. for approximately 18 h, until an OD of 1.5-1.6 was reached.

Single (10 mL) aliquots of 1×TYIR glucose or 1×TYIR alpha-cyclodextrin were individually inoculated with 1 mL of starter culture and were incubated for 24 h anaerobically, 32° C. After 24 h incubation, growth (turbidity) was observed in all three of the glucose-based cultures. This was repeated over multiple subcultures, showing (as expected) that glucose can support viable growth of all three of these bacterial types: N1-504, N1-4 (HMT) and *L. delbrueckii*. In contrast, after 24 h incubation in the alpha-cyclodextrin-based medium, no growth was observed for either of the *C. saccharoperbutylacetonicum* strains (N1-4 (HMT) or N1-504). The N1-4 (HMT) and N1-504 cultures were therefore incubated for a further 24 h but no viable cells were observed by microscopy. Meanwhile, after the initial 24 h incubation period, some growth was observed for *L. delbrueckii* on TYIR alpha-cyclodextrin. However, when this *L. delbrueckii* culture was used to inoculate a fresh aliquot of TYIR alpha-cyclodextrin (10% inoculum) and incubated for a further 24 h, visual inspection of the tube showed a reduction in turbidity, and a reduction in cell number compared to the inoculum culture was confirmed by microscopy.

This suggests that the initial appearance of some growth of *L. delbrueckii* was most likely due to substrate carryover from the starter culture and that the alpha-cyclodextrin-based medium does not support on-going growth of *L. delbrueckii*.

Taken together, these results show that alpha-cyclodextrin is unable to sustain growth of any of the three bacterial strains tested (*C. saccharoperbutylacetonicum* N1-4 (HMT), *C. saccharoperbutylacetonicum* N1-505 and *Lactobacillus delbrueckii*) when it is used as the main carbohydrate source.

Beta-cyclodextrin is poorly soluble in aqueous media. It was only possible to make a 1.5% (15 g/l) stock of beta-cyclodextrin. After combining with an equal volume of 2×TYIR nutrient stock the final beta-cyclodextrin concentration was only 7.5 g/I. The ability of *C. saccharoperbutylacetonicum* N1-4 (HMT) to grow on TYIR-beta-cyclodextrin was assessed, as above. Visual (turbidity) and microscope examination after repeated subculturing showed only a low density of bacterial cells, which appeared to be neither actively dividing, nor overly damaged (crumpled).

Example 3: Growth of *C. saccharoperbutylacetonicum* N1-4 (HMT) and N1-504 on Gamma-Cyclodextrin with Some Alpha-Cyclodextrin A 2×TYIR nutrient stock and individual 10% carbohydrate stocks (100 g/L) of gamma-cyclodextrin or alpha-cyclodextrin were prepared and sterilised separately for 15 min at 121° C. A standard volume of 2× nutrient stock (15 mL) was pipetted into sterile serum bottles with different volumes of 10% gamma-cyclodextrin and 10% alpha-cyclodextrin to give a working volume of 30 mL, with final concentrations of 1×TYIR and 5% total defined carbohydrate. The gamma- and alpha-cyclodextrin stocks were added to give ratios (mass:mass %) of γ:α 100:0 (gamma only control), 95:5 or 90:10. The bottles were incubated at 32° C. in an anaerobic cabinet for 24 h prior to inoculation with starter culture.

Starter cultures were prepared by inoculating 30 mL of pre-warmed, anaerobic RCM medium with an RCM-reconstituted *C. saccharoperbutylacetonicum* N1-4 (HMT) or N1-504 freeze-dried stock. Both cultures were incubated anaerobically at 32° C. for approximately 18 h, reaching an $OD_{600\,nm}$ of 1.7.

Triplicate screen bottles of TYIR gamma:alpha 100:0, TYIR gamma:alpha 95:5 or TYIR gamma:alpha 90:10 were inoculated with 3 mL of *C. saccharoperbutylacetonicum* N1-4 (HMT) or N1-504 starter cultures (5% inoculum). Cultures were incubated anaerobically at 32° C. for 75 h and sampled at 24 h, 48 h and 75 h by removing 1 mL from each bottle. Cell-free culture supernatants were analysed by HPLC to quantify residual carbohydrates (g/L) in the growth medium and production of acetone, ethanol and butanol (g/L).

Figure 2:
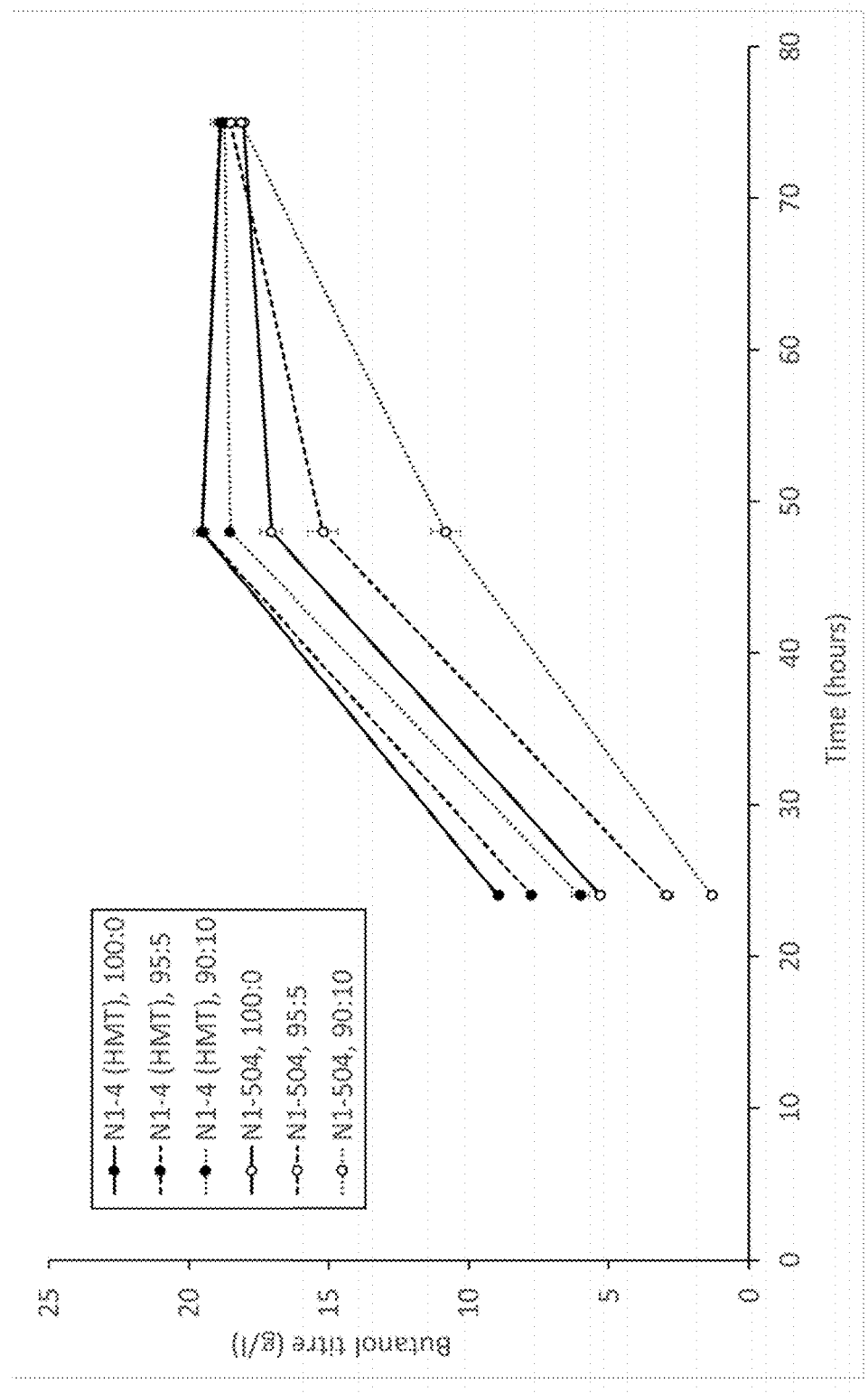
FIG. 2 shows the ability of two strains of *C. saccharoperbutylacetonicum* (N1-4 (HMT) and N1-504) to produce butanol when provided with gamma-cyclodextrin as the main carbohydrate source, and when some of the gamma-cyclodextrin is substituted with alpha-cyclodextrin (0%, 5% and 10% of total designated carbohydrate).

Butanol production is shown in FIG. 2. Both *C. saccharoperbutylacetonicum* strains were able to metabolise pure gamma-cyclodextrin (100:0) to produce ABE, giving final (75 h) titres of butanol (18.9 and 18.2 g/I for N1-4 (HMT) and N1-504, respectively) although N1-4 (HMT) actually achieved the highest butanol titre (19.5 g/l) at 48 h, while N1-504 produced butanol more slowly.

The presence of increasing proportion of alpha-cyclodextrin tended to correlate with slower butanol production. For the highest proportion of alpha (gamma:alpha=90:10) butanol titres at the earlier time points (24 h and 48 h) were significantly lower than those without alpha-cyclodextrin, although by 75 h these differences were small, indicating that the presence of alpha-cyclodextrin, which is often co-produced by CGTase enzymes with gamma-cyclodextrin, does not prohibit utilisation of gamma-cyclodextrin.

No significant differences in acetone or ethanol production were observed between the two strains. The presence of alpha-cyclodextrin did not affect acetone or ethanol production from either strain.

In summary, both *C. saccharoperbutylacetonicum* strains were able to metabolise gamma-cyclodextrin, and both strains produce butanol more slowly if some of the gamma-cyclodextrin is replaced by alpha-cyclodextrin.

Example 4: Testing Ability of Three Different *Clostridium* Species to Utilise Gamma-Cyclodextrin A 2×CGM nutrient stock (5 g/L yeast extract, 0.75 g/L $K_2HPO_4$, 0.75 g/L $KH_2PO_4$, 0.4 g/L $MgSO_4.7H_2O$, 10 mg/L $FeSO_4.7H_2O$, 10 mg/L $MnSO_4.4H_2O$, 1 g/L NaCl, 2 g/L $(NH_4)_2SO_4$ and 2 g/L asparagine) and individual 10% carbohydrate stocks (100 g/L) of glucose, gamma-cyclodextrin or alpha-cyclodextrin were prepared and sterilised separately for 15 min at 121° C. Equal volumes of 2× nutrient stock and 10% carbohydrate solution were pipetted into sterile 100 mL serum bottles to give a working volume of 60 mL, with final concentrations of 1×CGM and 5% defined carbohydrate. A small volume of 1×CGM (no added carbohydrate) was prepared for wash steps by mixing 2× stock with an equal volume of sterile RO (reverse osmosis-purified) water. The bottles were incubated at 32° C. in an anaerobic cabinet for 24 h prior to inoculation with starter culture.

Starter cultures were prepared for three different solventogenic *Clostridium* species by inoculating 30 mL lots of pre-warmed, anaerobic RCM medium with RCM-reconstituted freeze-dried stocks of *C. saccharoperbutylacetonicum* N1-4 (HMT), *C. beijerinckii* NCP260, or *C. acetobutylicum* ATCC 824. The cultures were then incubated anaerobically for approximately 18 h at 32° C. for *C. beijerinckii* and *C. saccharoperbutylacetonicum*, or 37° C. for *C. acetobutylicum*.

The starter culture was used to inoculate CGM glucose (10% inoculum) and incubated anaerobically at 32° C. (or 37° C. for *C. acetobutylicum*) for approximately 7 h. This subculture was used to inoculate a second CGM glucose aliquot which was incubated anaerobically (32° C. or 37° C.) for approximately 18 h. The cells were harvested by centrifugation (4000×g, 10 min, RT) and suspended in 60 mL of 1×CGM (no sugar) by pipetting to remove residual glucose carry-over. The suspension was centrifuged and the cells suspended as previously stated. Duplicate bottles of 1×CGM containing 5% glucose, gamma-cyclodextrin or alpha-cyclodextrin were inoculated with the cell suspension (10% inoculum). Cultures were incubated anaerobically at 32° C. for 72 h and sampled at 24 h, 48 h and 72 h by removing 1 mL from each bottle.

Cell-free culture supernatants were analysed by GC to quantify the fermentation products acetone, ethanol and butanol (g/L).

Figure 3A:
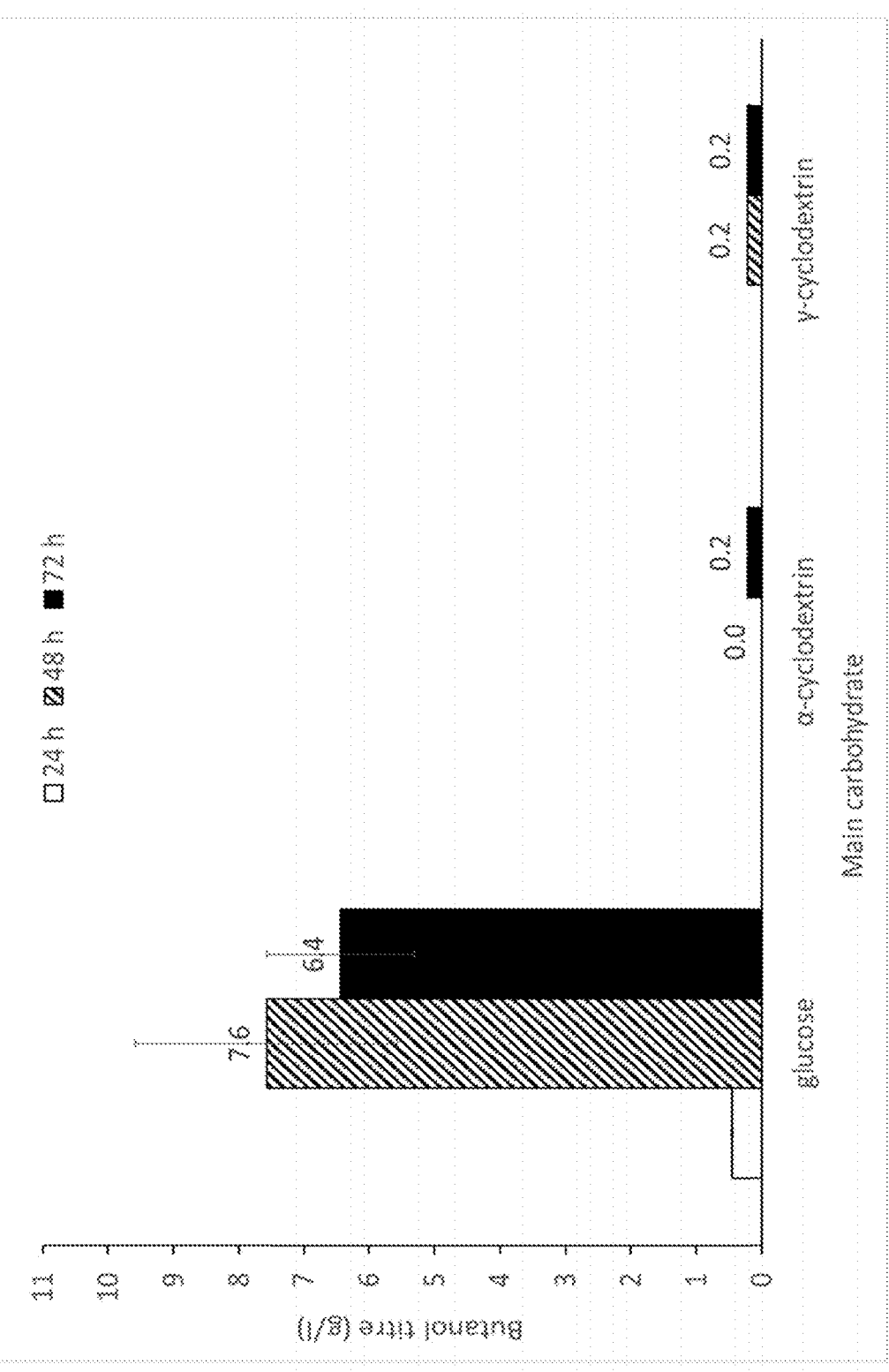
FIG. 3 shows butanol titres measured at 24, 48 and 72 hours in small-scale fermentations of three different carbohydrates (glucose, alpha-cyclodextrin and gamma-cyclodextrin) by three different *Clostridium* species: *C. acetobutylicum* (FIG. 3A), *C. beijerinckii* (FIG. 3B) and *C. saccharoperbutylacetonicum* (FIG. 3C).

*C. acetobutylicum* ATCC 824 grew well on glucose-based medium, with negligible appearance of growth (turbidity) in cultures based on either alpha- or gamma-cyclodextrin. This was supported by GC analysis, which showed that the major product, butanol, was only produced in significant amounts in the glucose-based cultures (FIG. 3A). Therefore neither alpha- nor gamma-cyclodextrin are readily fermentable by the *C. acetobutylicum*.

Figure 3B:
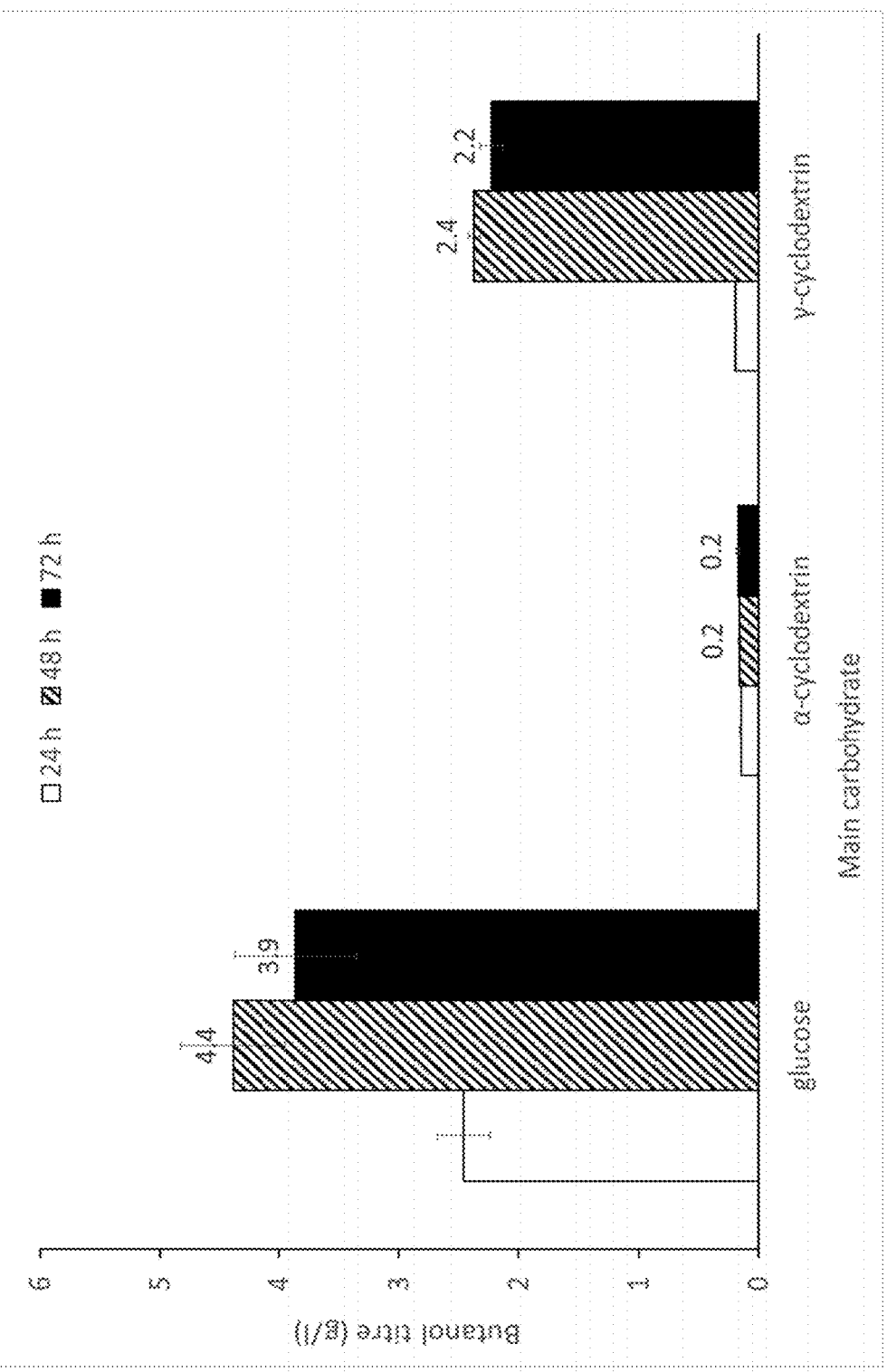

*C. beijerinckii* NCP260 grew on glucose, as expected, but growth (by eye) was negligible on alpha-cyclodextrin and poor on gamma-cyclodextrin. GC analysis showed that that titres for the major product, butanol were negligible on alpha-cyclodextrin. Some butanol was produced on gamma-cyclodextrin, but the 48 h titre on gamma-cyclodextrin was only 55% of the butanol titre on the equivalent glucose-based medium (FIG. 3B). Therefore, alpha-cyclodextrin is not readily fermentable, and gamma-cyclodextrin is only somewhat fermentable by the *C. beijerinckii*, compared to fermentation of glucose.

Figure 3C:
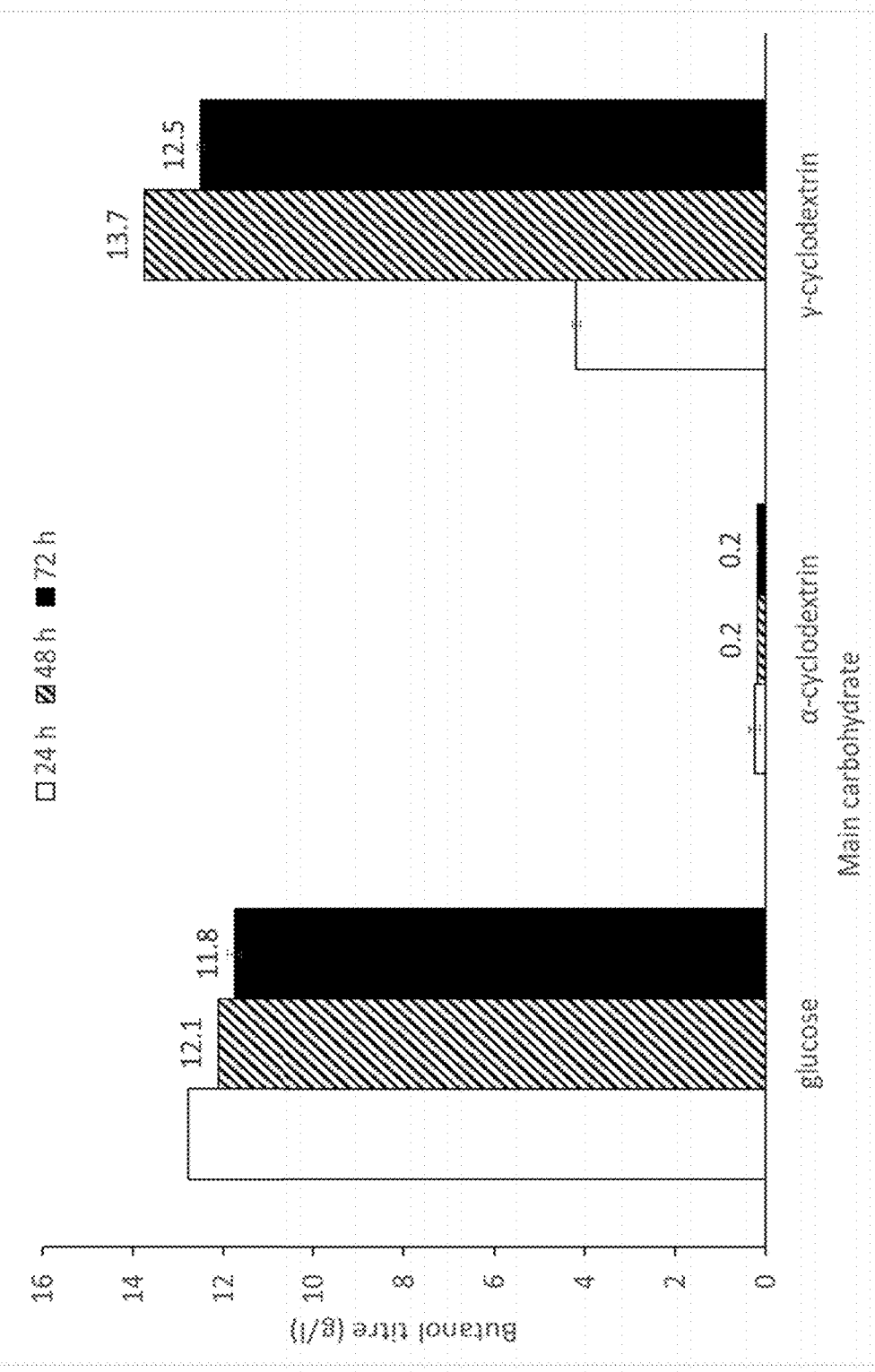

For *C. saccharoperbutylacetonicum* N1-4 (HMT) significant growth was observed by eye in the cultures based on glucose and surprisingly gamma-cyclodextrin, but not in the cultures based on alpha-cyclodextrin. Even more surprisingly, production of butanol was better in cultures grown on gamma-cyclodextrin than it was on glucose (butanol titres at 48 and 72 hours were higher with gamma-cyclodextrin than with glucose), e.g. FIG. 3C.

Example 5: *C. tyrobutyricum* Growth Test on Gamma-Cyclodextrin

*C. tyrobutyricum* ATCC 25755 was grown in 30 ml of pre-warmed RCM medium in a sealed serum bottle from reconstituted freeze-dried stocks for approximately 18 h at 37° C. 6 ml of this starter culture was then used to inoculate 54 ml aliquots of two media; (i) ¼ TYIR (2.5 g/L yeast extract, 2.5 g/L tryptone, 0.5 g/L $(NH_4)_2SO_4$, 0.1 g/L $FeSO_4.7H_2O$)+5% γ-cyclodextrin, and (ii) ¼ TYIR+5% glucose. These cultures were then incubated for ~7 hours under anaerobic conditions, after which 6 ml aliquots were used to inoculate second bottles of the same media which were incubated for another 18 hours.

In medium type (i), with γ-cyclodextrin as the carbon source, there was no visual appearance of growth (turbidity) after this time. Meanwhile in medium type (ii), with glucose as the carbon source, there was significant visual appearance of growth (turbidity) at 18 hours.

Example 6: Growth of *Pediococcus acidilactici* and *Lactobacillus casei* on Glucose and on Gamma-Cyclodextrin A 2×TYIR nutrient stock and individual 10% sugar stocks (100 g/L) of glucose or gamma-cyclodextrin were prepared and sterilised separately for 15 min at 121° C. Equal volumes of 2× nutrient stock and either 10% glucose or 10% gamma-cyclodextrin were pipetted into sterile 15 mL capacity polypropylene tubes to give a working volume of 10 mL, with final concentrations of 1×TYIR and 5% sugar in the media. The tubes were incubated at 32° C. in an anaerobic cabinet for 24 h prior to inoculation with starter culture.

Starter cultures were prepared by inoculating 10 mL of pre-warmed, anaerobic MRS medium with MRS-reconstituted *P. acidilactici* freeze-dried stock or *L. casei* freeze dried stock. Both cultures were incubated anaerobically at 32° C. for approximately 41 h, until healthy cultures were observed under the microscope.

10% subcultures were made from each starter culture, separately, into fresh lots of 10 mL 1×TYIR+5% glucose and also into 10 mL 1×TYIR+5% gamma-cyclodextrin. These were then incubated anaerobically at 32° C. for approximately 22-24 h and then samples of each were examined under the microscope and second 10% subcultures were prepared in the same types of fresh media and incubated under the same conditions. From these, final (third) 10% subcultures were prepared.

Cultures of both *P. acidilactici* and *L. casei* grown in 1×TYIR+5% glucose appeared visually turbid and produced gas following each subculture and incubation step. Microscopy also showed that cell density was higher in these at each subculture than those grown in 1×TYIR+5% gamma-cyclodextrin. Cultures grown in 1×TYIR+5% gamma-cyclodextrin did not appear turbid by eye and after the final subculture, very few cells were observed under the microscope, but these were not in an actively growing form (i.e. only individual or occasional pairs of cells were seen, whereas growing *Pediococcus acidilactici* and *Lactobacillus casei* cells would typically be in long chains) and can therefore possibly be attributed to carry-over of cells from a previous subculture.

In summary, *P. acidilactici* and *L. casei* both grew well in glucose-based medium, but not on gamma-cyclodextrin-based medium.

Example 7: Product Titres from *C. saccharoperbutylacetonicum* Derivatives that have been Engineered to Make Alternative Bio-Products are Enhanced when Grown on Gamma-Cyclodextrin Wildtype *C. saccharoperbutylacetonicum* N1-4 (HMT) (ATCC 27021) is engineered to create a derivative strain, which makes an alternative bio-product. In this example, this is done by knocking-out the bld gene (Genbank accession number WP_015395720), which encodes the enzyme converting butyryl-CoA to butyraldehyde (a precursor to butanol production). Consequently, the intermediate, butyryl-CoA, is then available for conversion to butyric acid, instead of to butanol.

Figure 4:
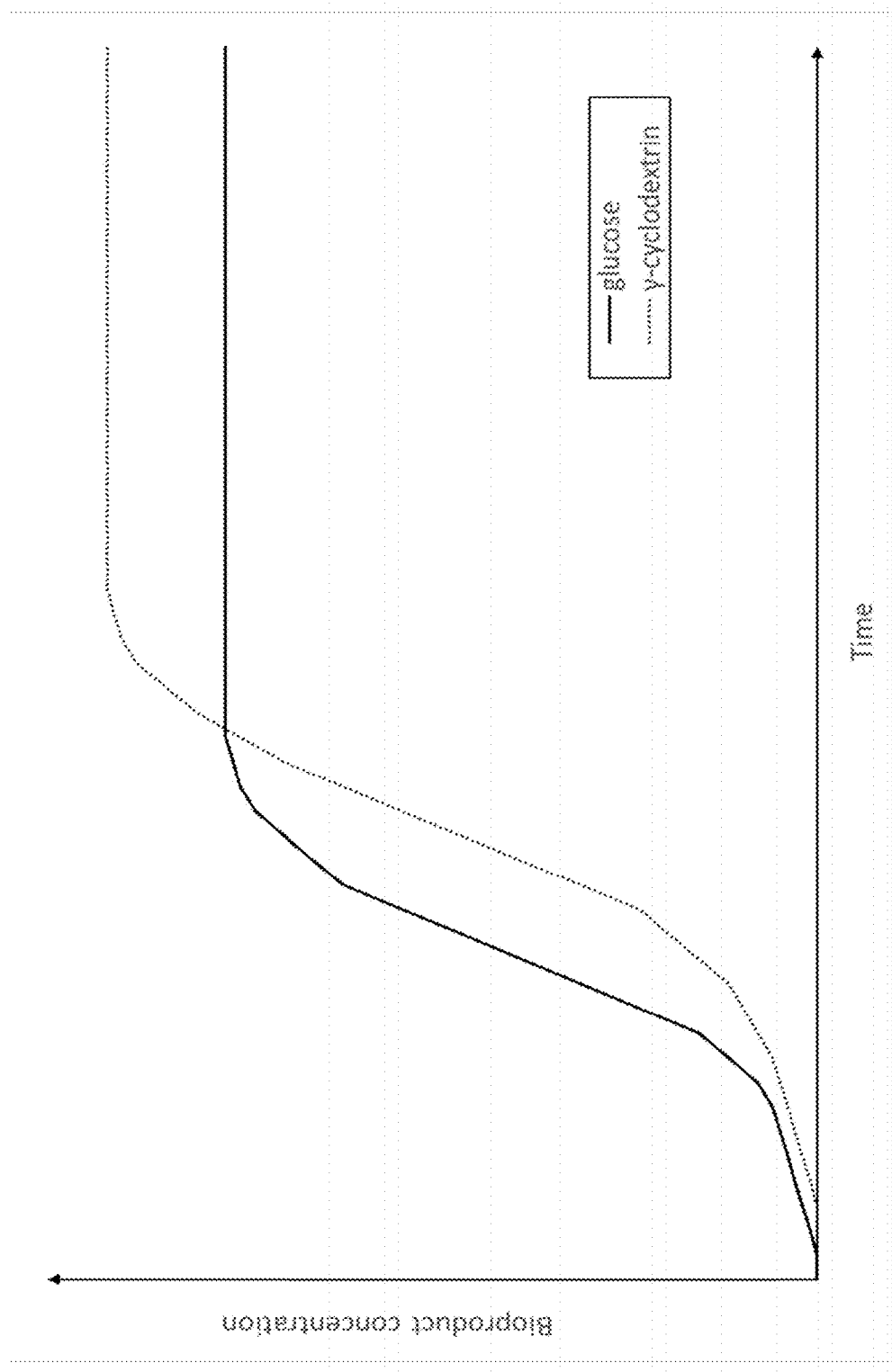
FIG. 4 shows the generation of a bio-product by a *C. saccharoperbutylacetonicum* derivative on two different carbohydrate sources (glucose and gamma-cyclodextrin).

The resulting strain "ATCC 27021-BA" is grown on glucose-based medium and on gamma-cyclodextrin-based medium (based on conditions described in Example 2). Levels of target bio-product (butyric acid) are measured by HPLC using standard conditions e.g. US 20122/76606A1 (Example 22)). FIG. 4 shows that ATCC 27021-BA achieves higher titres of bio-product (butyric acid) when grown on gamma-cyclodextrin compared to when it is grown on glucose.

Example 8: A *C. saccharoperbutylacetonicum* Derivative that has been Engineered to Make Alternative Bio-Products can Out-Compete Lactic Acid Bacteria when Grown on Gamma-Cyclodextrin A derivative of *C. saccharoperbutylacetonicum* ATCC 27021 is engineered to make an alternative bio-product, e.g. strain "ATCC 27021-BA" (described in Example 7). A competition study is set up based on methods described in Example 1. Essentially: Media are prepared with the main carbohydrate source being either glucose or gamma-cyclodextrin. These are inoculated with pre-cultures of *L. delbrueckii*, or the *C. saccharoperbutylacetonicum* derivative ATCC 27021-BA, or both. Cultures are incubated and levels of the key fermentation products are measured at multiple time points. Both strains individually grow well on glucose, each generating their main bio-product (lactic acid and butyric acid, from *L. delbrueckii* and ATCC 27021-BA, respectively). When both cultures are combined in glucose-based media, the *L. delbrueckii* outcompetes the *C. saccharoperbutylacetonicum* derivative, and the main product from this mixed inoculum is lactic acid. In contrast, when the mixed culture is used to inoculate gamma-cyclodextrin-based media, the *C. saccharoperbutylacetonicum* derivate outcompetes the *L. delbrueckii* and the main product is butyric acid. This is in keeping with experimental results seen in Example 1.

Figure 5:
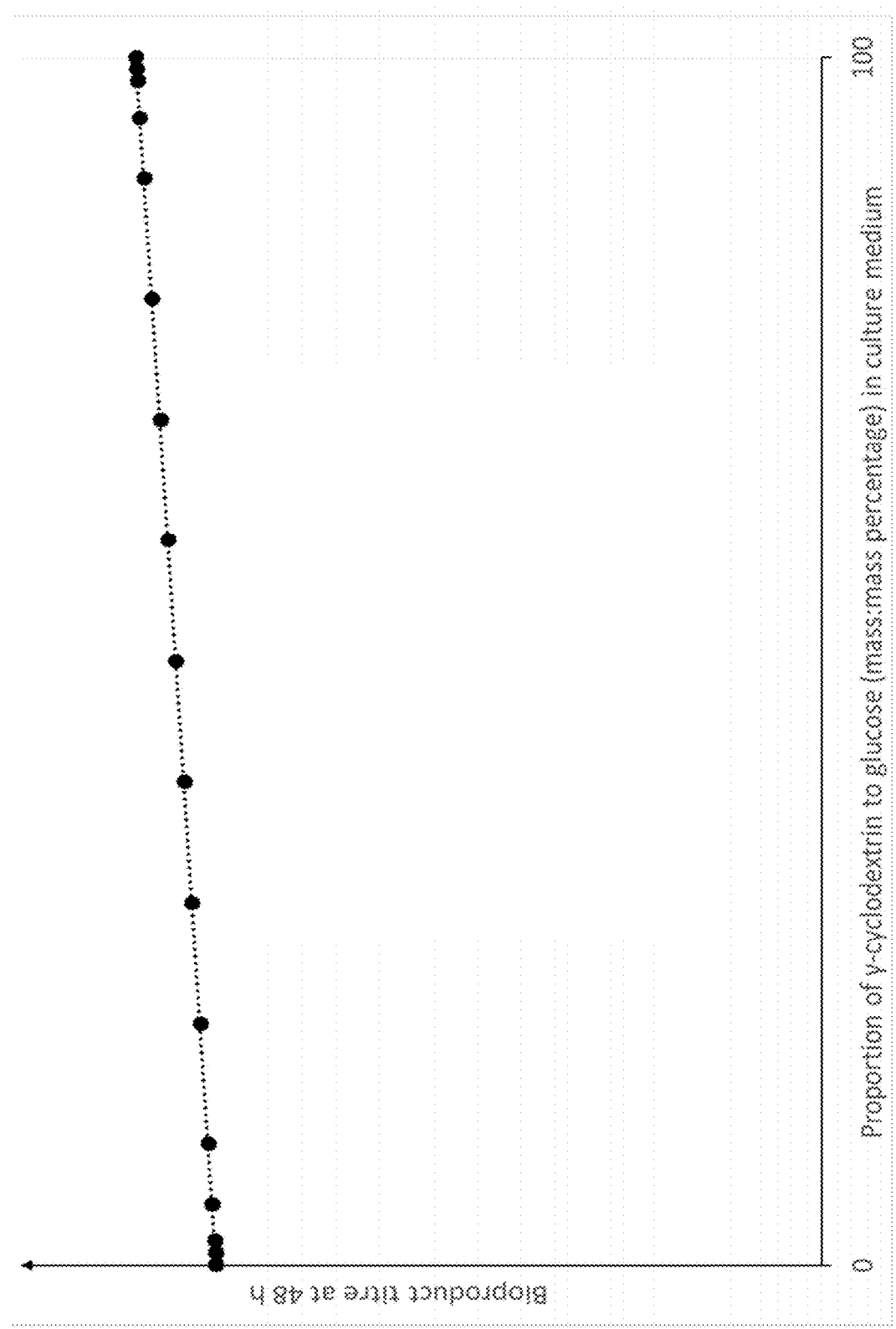
FIG. 5 shows the influence of the proportion of gamma-cyclodextrin to glucose on bio-product production.

Example 9: Increasing the Ratio of Gamma-Cyclodextrin to Glucose Results in Higher Bio-Product Titres Media are prepared as described in Example 3. This time, the defined carbohydrate portions are a range of different ratios of gamma-cyclodextrin to glucose, e.g. 0:100, 1:99, 2:98, 5:95, 10:90, 20:80, 30:70, 40:60, 50:50, 60:40, 70:30, 80:20, 90:10, 95:5, 98:2, 99:1 and 100:0. These are inoculated with *C. saccharoperbutylacetonicum* N1-4 (HMT), and incubated. Bio-product titres are measured at 48 hours (essentially as described in Example 3). The data show that increasing the proportion of gamma-cyclodextrin results in increased bio-product titre (FIG. 5).

Example 10: Study of *C. saccharoperbutylacetonicum* Wildtype and Sporulation-Deficient Mutant on Gamma-Cyclodextrin To reduce sporulation while retaining butanol production, a mutation was introduced into the *C. saccharoperbutylacetonicum* N1-4 (HMT) gene for Spo0A (located in the genome), changing isoleucine 261 to threonine. This was done utilising genome editing technology described in WO2015/159087. The nucleotide mutation necessary for this change in amino acid sequence was confirmed by High Resolution Melting (HRM) followed by Sanger sequencing.

The wildtype protein sequence for the Spo0A protein of *C. saccharoperbutylacetonicum* N1-4(HMT) is in NCBI sequence ID WP_015392838.1. A picture of this wildtype 273 amino acid sequence is shown in FIG. 6A, where residue I261 is indicated with a box. (This sequence is also provided as SEQ ID NO: 1.)

The I261T mutant was generated by editing the gene for Spo0A as follows: the nucleotide sequence of the codon that encodes isoleucine 261, ATT, was changed to the nucleotide sequence ACT, which encodes threonine. The resulting amino acid sequence of Spo0A I261T is shown in FIG. 6B, where residue 261, now a 'T', is indicated with a box. (This sequence is also provided as SEQ ID NO: 2.) (Nucleotide sequences of the wildtype and I261T Spo0A gene are provided as SEQ ID NO: 3 and SEQ ID NO: 4, respectively.)

Figure 7:
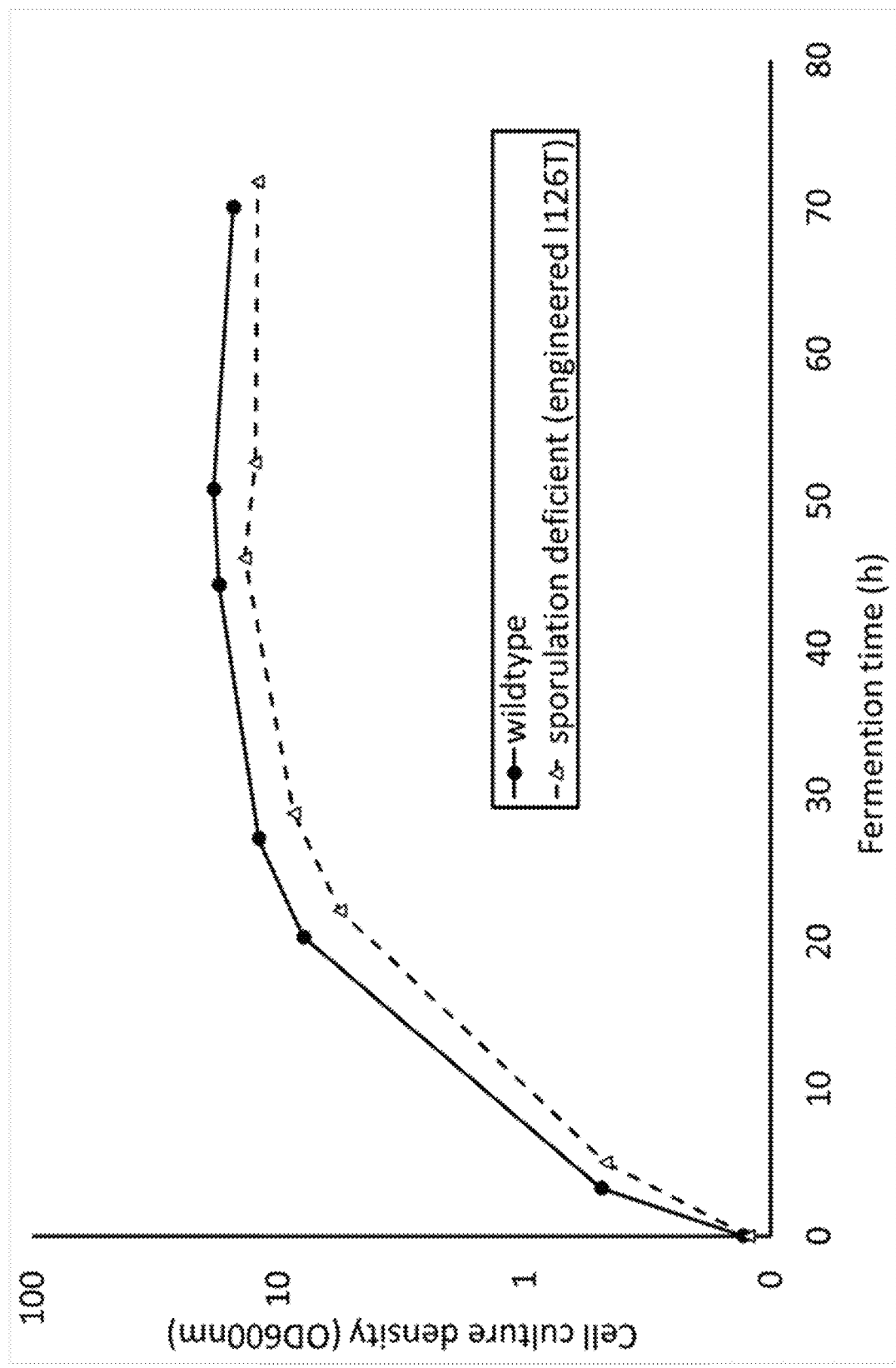
FIG. 7: Graph showing growth of wildtype and Spo0A I1261 cultures on gamma cyclodextrin.

The performances of wildtype *C. saccharoperbutylacetonicum* N1-4 (HMT) and the spo0A I126T derivative of *C. saccharoperbutylacetonicum* N1-4 (HMT) were examined on gamma cyclodextrin using bottle cultures, as follows:

Bottle cultures were prepared in 100 ml serum bottles containing 54 ml of sterilised medium (¼ TYIR (625 mg/L yeast extract, 6255 mg/L tryptone, 6.25 mg/L FeSO$_4$.7H$_2$O, and 125 mg/L (NH$_4$)$_2$SO$_4$)+50 g/l gamma cyclodextrin+100 mM MES buffer, pH of the medium adjusted to 6.5 after autoclaving), pre-equilibrated at 32° C. and inoculated with 6 ml pre-culture (also grown in ¼ TYIR+100 mM MES buffer+50 g/l gamma cyclodextrin, pH 6.5). These were set up in triplicate for wildtype *C. saccharoperbutylacetonicum* N1-4 (HMT) and for the spo0A I126T derivative engineered from *C. saccharoperbutylacetonicum* N1-4 (HMT). A t=0 sample was taken immediately and the cultures were then incubated at 32° C. in an anaerobic cabinet. Multiple samples were taken over the next 72 hours. Samples were analysed by microscopy (bright field microscope, 40× magnification) to look for sporulation. Spores were seen as "phase-bright" regions within the bacteria. The optical density of samples was determined using a spectrophotometer at 600 nm and, if necessary, diluting the sample with fresh medium to ensure the reading was within the linear range of the spectrophotometer. The concentrations of gamma cyclodextrin, butanol, other solvents and organic acids were determined for clarified samples (i.e. after cells had been removed by centrifugation) using standard HPLC and sometimes GC methods. Both the wildtype and spo0A 1126T cultures grew well on gamma cyclodextrin, as shown by the optical density graph in FIG. 7.

Figure 8:
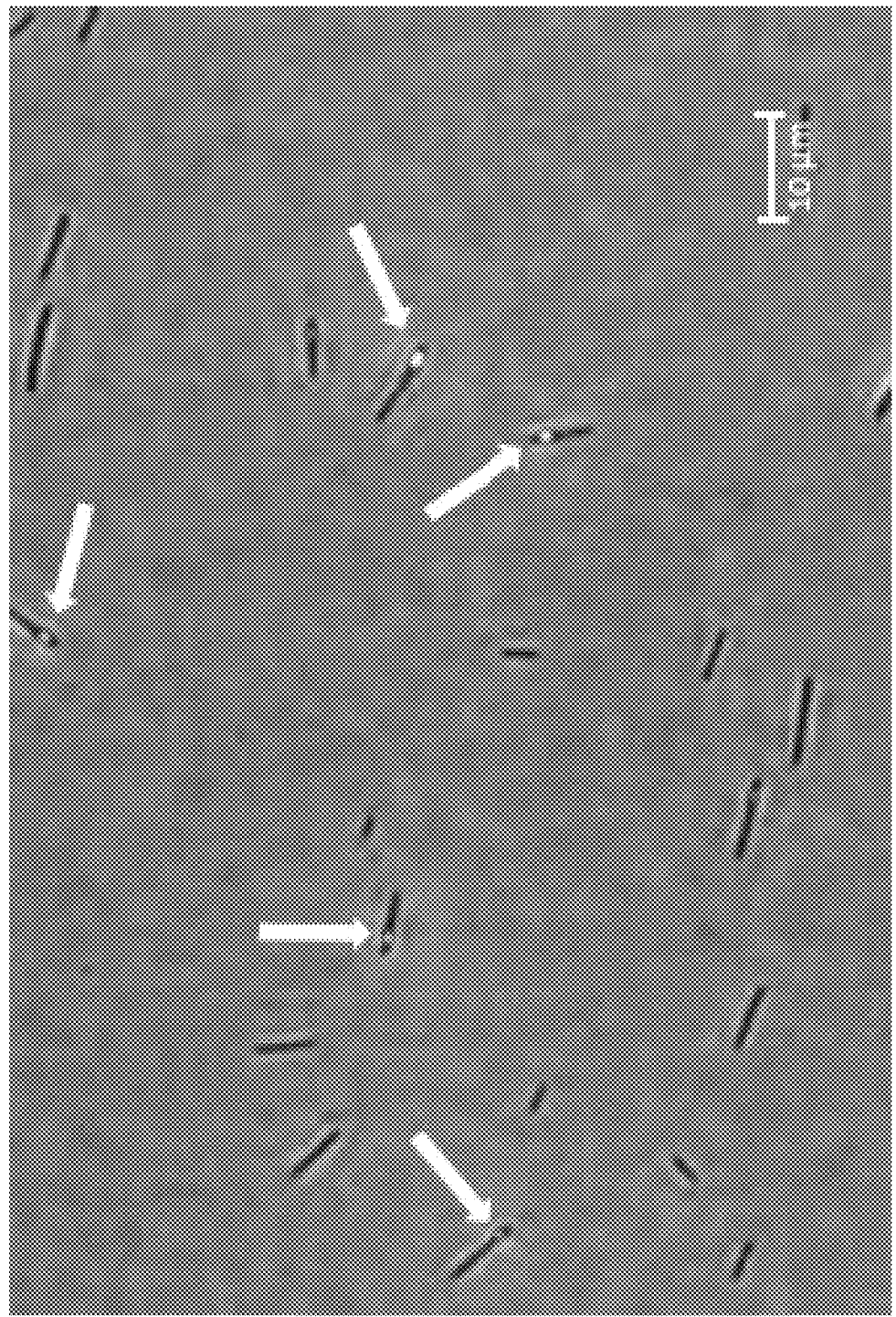
FIG. 8: Microscope picture of a culture of wildtype *C. saccharoperbutylacetonicum* N1-4 (HMT) grown on gamma-cyclodextrin for 20 hours. Phase-bright spores were already seen by this time, indicated by the white arrows.
Figure 9:
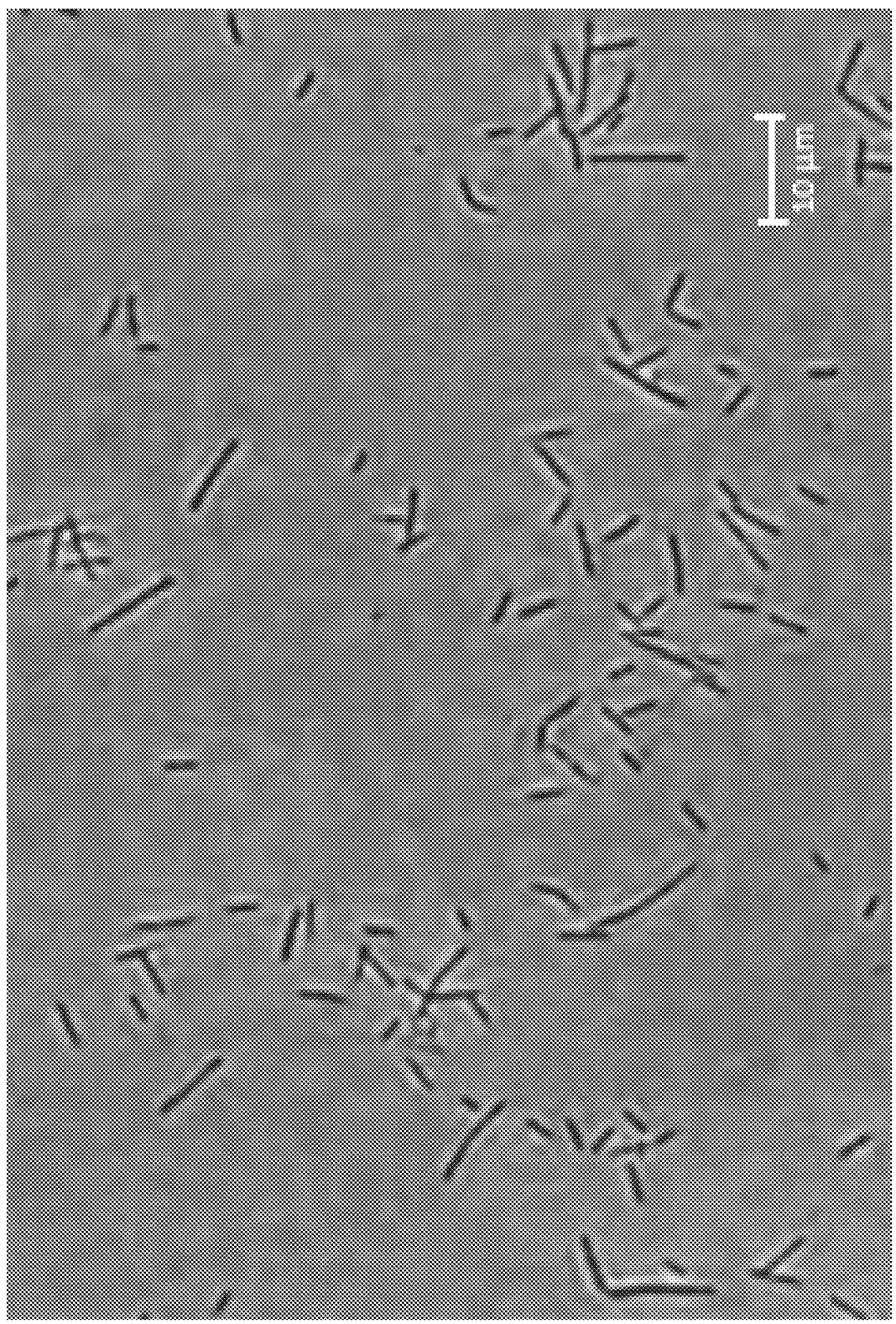
FIG. 9: Microscope picture of a culture of spo0A I1261 mutant of *C. saccharoperbutylacetonicum* N1-4 (HMT) grown on gamma-cyclodextrin for 72 hours. No phase-bright spores were seen.

When grown on gamma-cyclodextrin, wildtype cells were seen to sporulate as early as 20 hours (FIG. 8). Meanwhile the cultures of the spo0A I126T mutant of *C. saccharoperbutylacetonicum* N1-4 (HMT) culture did not contain spores, even as late as 72 hours (FIG. 9).

Figure 10:
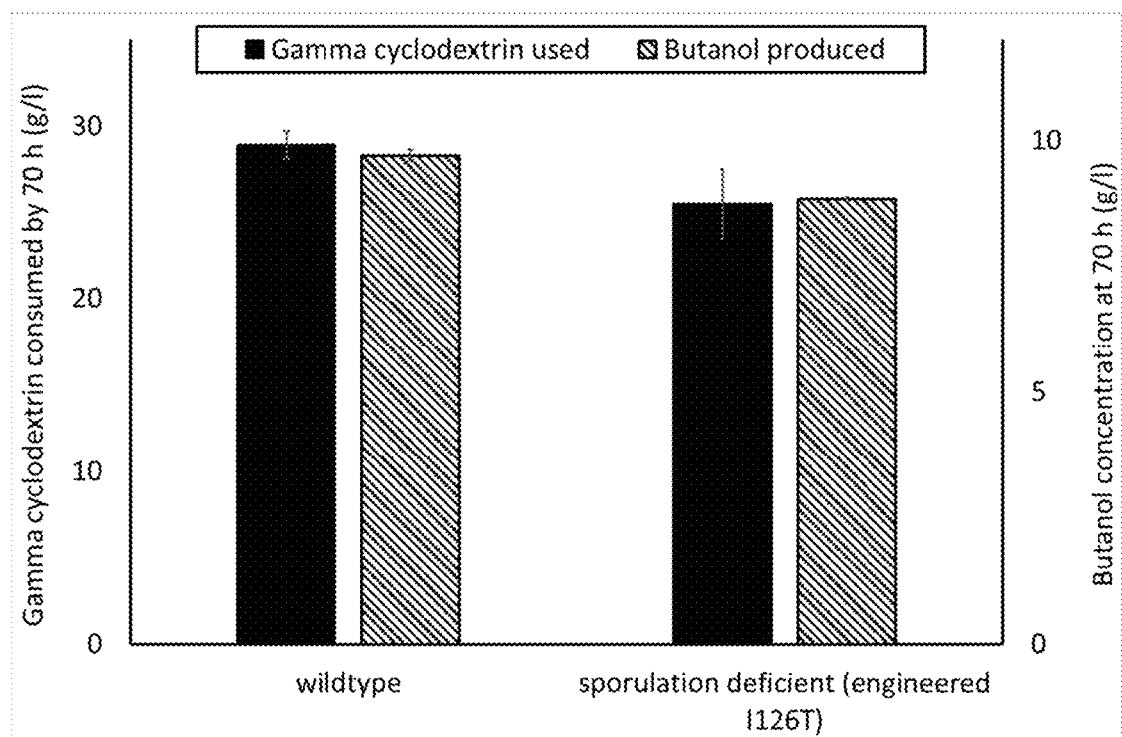
FIG. 10: Graph showing consumption of gamma-cyclodextrin and production of butanol by wildtype and spo0A I1261 *C. saccharoperbutylacetonicum* N1-4 (HMT).

HPLC analysis showed that both the wildtype and Spo0A 1126T cultures consumed gamma-cyclodextrin and produced butanol (FIG. 10).

This Example demonstrates that sporulation-deficient derivatives of *C. saccharoperbutylacetonicum* can still grow on gamma-cyclodextrin and produce solvents, but no longer can readily sporulate on gamma-cyclodextrin.

SEQUENCES

SEQ ID NO: 1 Amino acid sequence of wildtype Spo0A
MEDSKISVLIADDNKEFCSILNDYLLNQKDIVVTGIAKDGREALDLIVER
KPDLVILDIIMPHLDGLGVLEKLNTMNLEKVPRIIILSAVGQDKITQQAI
TLGADYYTVKPFDMEVFTKRIREMENGAPAQESNVRASSYMQSPVMTSGE
PKSKTPVDLETEITNIIHEVGVPAHIKGYMYLREAITMVVNDMELLSAVT
KELYPSIAKKYNTTASRVERAIRHAIEVAWGRGQIDAINRLFGYTVHTEK
GKPTNSEFIAIIADKLRLKNKVS SEQ ID NO: 2 Amino acid sequence of I261T Spo0A
MEDSKISVLIADDNKEFCSILNDYLLNQKDIVVTGIAKDGREALDLIVER
KPDLVILDIIMPHLDGLGVLEKLNTMNLEKVPRIIILSAVGQDKITQQAI
TLGADYYTVKPFDMEVFTKRIREMENGAPAQESNVRASSYMQSPVMTSGE
PKSKTPVDLETEITNIIHEVGVPAHIKGYMYLREAITMVVNDMELLSAVT
KELYPSIAKKYNTTASRVERAIRHAIEVAWGRGQIDAINRLFGYTVHTEK
GKPTNSEFIATIADKLRLKNKVS SEQ ID NO: 3 Nucleotide sequence of wildtype Spo0A
atggaagattcaaaaatatctgtacttattgccgatgataacaaagaatt
ttgtagcattttaaatgattacttattaaaccaaaaggatatcgttgtca
ctggtattgcaaaagatggtagagaagcctagatttgattgtagagaga
aagcctgatttagttattctagatataattatgcctcatttagacggact
aggagttttagaaaaattaaatacaatgaatttagaaaaagttccaagaa
taataatactatctgcagttgggcaagataaaataactcaacaagctata
actcttggtgcagattattatactgtaaagccttttgatatggaagtatt
cactaagagaataagagaaatgttcaatggggctccagcgcaagaatcta
atgttagagcaagttcatatatgcaatcaccagtaatgacttctggtgaa
ccaaaatcaaaaacaccagtagatttagaaacagaaattactaatatcat
acatgaagttggcgttccagctcatattaaaggttatatgtatttaagag
aagctataactatggtagtaaacgatatggagctattatcagcagtaaca
aaggaattatatccttcaatagctaagaagtacaatacaacagcttcaag
agtagaaagagctataagacatgcaatagaagttgcatggggtagaggac
aaatagatgctattaatagactatttggatatactgttcatacagaaaaa
ggtaaacctacaaatagtgaatttatcgctatatcgctgataagcttcg
tttgaaaaacaaggttagctag SEQ ID NO: 4 Nucleotide sequence of I261T Spo0A
atggaagattcaaaaatatctgtacttattgccgatgataacaaagaatt
ttgtagcattttaaatgattacttattaaaccaaaaggatatcgttgtca
ctggtattgcaaaagatggtagagaagcctagatttgattgtagagaga
aagcctgatttagttattctagatataattatgcctcatttagacggact
aggagttttagaaaaattaaatacaatgaatttagaaaaagttccaagaa
taataatactatctgcagttgggcaagataaaataactcaacaagctata
actcttggtgcagattattatactgtaaagccttttgatatggaagtatt
cactaagagaataagagaaatgttcaatggggctccagcgcaagaatcta
atgttagagcaagttcatatatgcaatcaccagtaatgacttctggtgaa
ccaaaatcaaaaacaccagtagatttagaaacagaaattactaatatcat
acatgaagttggcgttccagctcatattaaaggttatatgtatttaagag
aagctataactatggtaaacgatatggagctattatcagcagtaaca
aaggaattatatccttcaatagctaagaagtacaatacaacagcttcaag
agtagaaagagctataagacatgcaatagaagttgcatggggtagaggac
aaatagatgctattaatagactatttggatatactgttcatacagaaaaa
ggtaaacctacaaatagtgaatttatcgctactatcgctgataagcttcg
tttgaaaaacaaggttagctag

The invention claimed is:

1. A process for producing one or more organic solvent(s) selected from the group consisting of n-butanol, ethanol and acetone, the process comprising the steps:
   (a) culturing *Clostridium saccharoperbutylacetonicum* cells in a liquid culture medium in a culture vessel, wherein the *Clostridium saccharoperbutylacetonicum* cells are capable of producing one or more organic solvent(s) selected from the group consisting of n-butanol, ethanol and acetone, wherein the *Clostridium saccharoperbutylacetonicum* cells are capable of utilizing gamma-cyclodextrin as a carbon source, and wherein the culture medium comprises or is fed gamma-cyclodextrin as a carbon source and optionally one or more other carbon sources, and optionally
   (b) harvesting and/or purifying one or more organic solvent(s) selected from the group consisting of n-butanol, ethanol and acetone from the *Clostridium saccharoperbutylacetonicum* cells or from the culture medium.

2. A process as claimed in claim 1, wherein the *Clostridium saccharoperbutylacetonicum* is sporulation-deficient.

3. A process as claimed in claim 2, wherein the *Clostridium saccharoperbutylacetonicum* has one or more mutations in a gene associated with sporogenesis or a spo gene, which renders the *Clostridium saccharoperbutylacetonicum* sporulation-deficient.

4. A process as claimed in claim 3, wherein the gene associated with sporogenesis is spo0A.

5. A process as claimed in claim 4, wherein the spo0A gene has a mutation which codes for threonine at the position which corresponds to position 261 of SEQ ID NO: 1.

6. A process as claimed in claim 1, wherein gamma-cyclodextrin is the primary utilizable carbon source in the culture medium or being fed to the culture medium.

7. A process as claimed in claim 1, wherein the culture medium at the start of the process or during the process comprises 0.5-20% gamma-cyclodextrin.

8. A process as claimed in claim 1, wherein the culture medium at the start of the process or during the process comprises less than 10% utilizable or assimilable carbon-sources other than cyclodextrins.

9. A process as claimed in claim 1, wherein the *Clostridium saccharoperbutylacetonicum* are solventogenic and/or monophasic.

10. A process as claimed in claim 1, wherein the *Clostridium saccharoperbutylacetonicum* is a N1-strain, or a monophasic and solventogenic variant or derivative thereof.

* * * * *

SEQUENCE LISTING

<160> NUMBER OF SEQ ID NOS: 4

<210> SEQ ID NO 1
<211> LENGTH: 273
<212> TYPE: PRT
<213> ORGANISM: Clostridium saccharoperbutylacetonicum

<400> SEQUENCE: 1

Met Glu Asp Ser Lys Ile Ser Val Leu Ile Ala Asp Asp Asn Lys Glu
1               5                   10                  15

Phe Cys Ser Ile Leu Asn Asp Tyr Leu Leu Asn Gln Lys Asp Ile Val
            20                  25                  30

Val Thr Gly Ile Ala Lys Asp Gly Arg Glu Ala Leu Asp Leu Ile Val
        35                  40                  45

Glu Arg Lys Pro Asp Leu Val Ile Leu Asp Ile Ile Met Pro His Leu
    50                  55                  60

Asp Gly Leu Gly Val Leu Glu Lys Leu Asn Thr Met Asn Leu Glu Lys
65                  70                  75                  80

Val Pro Arg Ile Ile Ile Leu Ser Ala Val Gly Gln Asp Lys Ile Thr
                85                  90                  95

```
Gln Gln Ala Ile Thr Leu Gly Ala Asp Tyr Tyr Thr Val Lys Pro Phe
            100                 105                 110

Asp Met Glu Val Phe Thr Lys Arg Ile Arg Glu Met Phe Asn Gly Ala
        115                 120                 125

Pro Ala Gln Glu Ser Asn Val Arg Ala Ser Ser Tyr Met Gln Ser Pro
    130                 135                 140

Val Met Thr Ser Gly Glu Pro Lys Ser Lys Thr Pro Val Asp Leu Glu
145                 150                 155                 160

Thr Glu Ile Thr Asn Ile Ile His Glu Val Gly Val Pro Ala His Ile
                165                 170                 175

Lys Gly Tyr Met Tyr Leu Arg Glu Ala Ile Thr Met Val Val Asn Asp
            180                 185                 190

Met Glu Leu Leu Ser Ala Val Thr Lys Glu Leu Tyr Pro Ser Ile Ala
        195                 200                 205

Lys Lys Tyr Asn Thr Thr Ala Ser Arg Val Glu Arg Ala Ile Arg His
    210                 215                 220

Ala Ile Glu Val Ala Trp Gly Arg Gly Gln Ile Asp Ala Ile Asn Arg
225                 230                 235                 240

Leu Phe Gly Tyr Thr Val His Thr Glu Lys Gly Lys Pro Thr Asn Ser
                245                 250                 255

Glu Phe Ile Ala Ile Ala Asp Lys Leu Arg Leu Lys Asn Lys Val
            260                 265                 270

Ser

<210> SEQ ID NO 2
<211> LENGTH: 273
<212> TYPE: PRT
<213> ORGANISM: Artificial Sequence
<220> FEATURE:
<223> OTHER INFORMATION: Clostridium saccharoperbutylacetonicum sequence
      with I261T mutation

<400> SEQUENCE: 2

Met Glu Asp Ser Lys Ile Ser Val Leu Ile Ala Asp Asn Lys Glu
1               5                   10                  15

Phe Cys Ser Ile Leu Asn Asp Tyr Leu Leu Asn Gln Lys Asp Ile Val
            20                  25                  30

Val Thr Gly Ile Ala Lys Asp Gly Arg Glu Ala Leu Asp Leu Ile Val
        35                  40                  45

Glu Arg Lys Pro Asp Leu Val Ile Leu Asp Ile Ile Met Pro His Leu
    50                  55                  60

Asp Gly Leu Gly Val Leu Glu Lys Leu Asn Thr Met Asn Leu Glu Lys
65                  70                  75                  80

Val Pro Arg Ile Ile Ile Leu Ser Ala Val Gly Gln Asp Lys Ile Thr
                85                  90                  95

Gln Gln Ala Ile Thr Leu Gly Ala Asp Tyr Tyr Thr Val Lys Pro Phe
            100                 105                 110

Asp Met Glu Val Phe Thr Lys Arg Ile Arg Glu Met Phe Asn Gly Ala
        115                 120                 125

Pro Ala Gln Glu Ser Asn Val Arg Ala Ser Ser Tyr Met Gln Ser Pro
    130                 135                 140

Val Met Thr Ser Gly Glu Pro Lys Ser Lys Thr Pro Val Asp Leu Glu
145                 150                 155                 160

Thr Glu Ile Thr Asn Ile Ile His Glu Val Gly Val Pro Ala His Ile
                165                 170                 175
```

```
Lys Gly Tyr Met Tyr Leu Arg Glu Ala Ile Thr Val Val Asn Asp
            180                 185                 190
Met Glu Leu Leu Ser Ala Val Thr Lys Glu Leu Tyr Pro Ser Ile Ala
        195                 200                 205
Lys Lys Tyr Asn Thr Thr Ala Ser Arg Val Glu Arg Ala Ile Arg His
        210                 215                 220
Ala Ile Glu Val Ala Trp Gly Arg Gly Gln Ile Asp Ala Ile Asn Arg
225                 230                 235                 240
Leu Phe Gly Tyr Thr Val His Thr Glu Lys Gly Lys Pro Thr Asn Ser
                245                 250                 255
Glu Phe Ile Ala Thr Ile Ala Asp Lys Leu Arg Leu Lys Asn Lys Val
            260                 265                 270
Ser

<210> SEQ ID NO 3
<211> LENGTH: 822
<212> TYPE: DNA
<213> ORGANISM: Clostridium saccharoperbutylacetonicum

<400> SEQUENCE: 3
atggaagatt caaaaatatc tgtacttatt gccgatgata caaagaatt ttgtagcatt      60 ttaaatgatt acttattaaa ccaaaaggat atcgttgtca ctggtattgc aaaagatggt    120
agagaagcct tagatttgat tgtagagaga aagcctgatt tagttattct agatataatt    180
atgcctcatt tagacggact aggagtttta gaaaaattaa atacaatgaa tttagaaaaa    240
gttccaagaa taataatact atctgcagtt gggcaagata aaataactca acaagctata    300
actcttggtg cagattatta tactgtaaag cctttttgata tggaagtatt cactaagaga    360
ataagagaaa tgttcaatgg ggctccagcg caagaatcta atgttagagc aagttcatat    420
atgcaatcac cagtaatgac ttctggtgaa ccaaaatcaa aaacaccagt agatttagaa    480
acagaaatta ctaatatcat acatgaagtt ggcgttccag ctcatattaa aggttatatg    540
tatttaagag aagctataac tatggtagta acgatatgg agctattatc agcagtaaca    600
aaggaattat atccttcaat agctaagaag tacaatacaa cagcttcaag agtagaaaga    660
gctataagac atgcaataga agttgcatgg ggtagaggac aaatagatgc tattaataga    720
ctatttggat atactgttca tacagaaaaa ggtaaaccta caaatagtga atttatcgct    780
attatcgctg ataagcttcg tttgaaaaac aaggttagct ag                         822

<210> SEQ ID NO 4
<211> LENGTH: 822
<212> TYPE: DNA
<213> ORGANISM: Artificial Sequence
<220> FEATURE:
<223> OTHER INFORMATION: Clostridium saccharoperbutylacetonicum sequence
      with I261T mutation

<400> SEQUENCE: 4
atggaagatt caaaaatatc tgtacttatt gccgatgata caaagaatt ttgtagcatt      60 ttaaatgatt acttattaaa ccaaaaggat atcgttgtca ctggtattgc aaaagatggt    120
agagaagcct tagatttgat tgtagagaga aagcctgatt tagttattct agatataatt    180
atgcctcatt tagacggact aggagtttta gaaaaattaa atacaatgaa tttagaaaaa    240
gttccaagaa taataatact atctgcagtt gggcaagata aaataactca acaagctata    300
actcttggtg cagattatta tactgtaaag cctttttgata tggaagtatt cactaagaga    360
```

```
ataagagaaa tgttcaatgg ggctccagcg caagaatcta atgttagagc aagttcatat    420
atgcaatcac cagtaatgac ttctggtgaa ccaaaatcaa aaacaccagt agatttagaa    480
acagaaatta ctaatatcat acatgaagtt ggcgttccag ctcatattaa aggttatatg    540
tatttaagag aagctataac tatggtagta aacgatatgg agctattatc agcagtaaca    600
aaggaattat atccttcaat agctaagaag tacaatacaa cagcttcaag agtagaaaga    660
gctataagac atgcaataga agttgcatgg ggtagaggac aaatagatgc tattaataga    720
ctatttggat atactgttca tacagaaaaa ggtaaaccta caaatagtga atttatcgct    780
actatcgctg ataagcttcg tttgaaaaac aaggttagct ag                       822
```